US009914955B2

(12) United States Patent
Stawarski et al.

(10) Patent No.: US 9,914,955 B2
(45) Date of Patent: Mar. 13, 2018

(54) GENETICALLY ENCODED FRET-BASED MMP-9 ACTIVITY BIOSENSOR AND USE THEREOF

(71) Applicant: Instytut Biologii Doświadczalnej im. Marcelego Nenckiego Polska Akademia Nauk, Warsaw (PL)

(72) Inventors: Michal Stawarski, Podkowa Leśna (PL); Jakub Wlodarczyk, Warsaw (PL); Leszek Kaczmarek, Warsaw (PL)

(73) Assignee: Instytut Biologii Doświadczalnej im. Marcelego Nenckiego Polska Akademia Nauk, Warsaw (PL)

(*) Notice: Subject to any disclaimer, the term of this patent is extended or adjusted under 35 U.S.C. 154(b) by 56 days.

(21) Appl. No.: 14/911,821

(22) PCT Filed: Aug. 12, 2014

(86) PCT No.: PCT/IB2014/063883
§ 371 (c)(1),
(2) Date: Feb. 12, 2016

(87) PCT Pub. No.: WO2015/022646
PCT Pub. Date: Feb. 19, 2015

(65) Prior Publication Data
US 2016/0194681 A1    Jul. 7, 2016

(30) Foreign Application Priority Data

Aug. 12, 2013  (PL) .......................... 405046

(51) Int. Cl.
| | |
|---|---|
| *A61K 39/00* | (2006.01) |
| *C07K 14/00* | (2006.01) |
| *C07K 16/00* | (2006.01) |
| *C12Q 1/37* | (2006.01) |
| *G01N 33/542* | (2006.01) |

(52) U.S. Cl.
CPC .............. *C12Q 1/37* (2013.01); *C07K 14/00* (2013.01); *G01N 33/542* (2013.01); *C07K 2319/50* (2013.01); *C07K 2319/60* (2013.01); *G01N 2333/96494* (2013.01)

(58) Field of Classification Search
CPC ............. C07K 14/00; C07K 2319/50; C07K 2319/60; G01N 33/542; G01N 2333/96494
USPC ............................ 530/300, 402; 424/192.1
See application file for complete search history.

(56) References Cited

U.S. PATENT DOCUMENTS

2009/0170194 A1   7/2009  Campbell et al.

FOREIGN PATENT DOCUMENTS

| WO | 2008019123 A2 | 2/2008 |
| WO | 2010017203 A1 | 2/2010 |
| WO | 2010150862 A1 | 12/2010 |

OTHER PUBLICATIONS

Kotterman et al., 2014, Nature Reviews, vol. 15, p. 445-451.*
Kodama et al., 2006, Current Medicinal Chemistry, vol. 13, p. 2155-2161.*
Takahashi et al., 2012, Frontiers in Bioscience, vol. S4, p. 133-141.*
Kaur et al., 2009, Current Gene Therapy, vol. 9. p. 434-458.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Namdev et al., 2016, Research J. Pharm. and Tech., 9(3), p. 305-312.*
Rehman et al., 2016, Current Drug targets, vol. 17, p. 1172-1188.*
Violin et al., "A genetically encoded fluorescent reporter reveals oscillatory phosphorylation by protein kinase C" The Journal of Cell Biology, vol. 161, No. 5, pp. 899-909, (Jun. 2003).
Michaluk et al. "beta-Dystroglycan as a Target for MMP-9, in Response to Enhanced Neuronal Activity", Journal of Biological Chemistry, pp. 16036-16041, vol. 282, No. 22 (Jun. 2007).
Yu et al.,"Cell surface-localized matrix metalloproteinase-9 proteolytically activates TGF-b and promotes tumor invasion and angiogenesis" Genes & Development, pp. 163-176, vol. 14, (Sep. 2000).
Day et al.,"Characterization of an improved donor fluorescent protein for Förster resonance energy transfer microscopy", J Biomed Opt., pp. 1-18, vol. 13, No. 3 (Jul. 2008).
Chen, "Design Genetic Fluorescent Probes to Detect Protease Activity and Calcium-Dependent Protein-Protein Interactions in Living Cells", Dissertation, Georgia State University, pp. 1-331, (Dec. 2008).
Akers et al.,"Detection of MMP-2 and MMP-9 activity in vivo with a triplehelical peptide optical probe" Bioconjug Chem., pp. 656-663, vol. 23, No. 3 (Mar. 2012).
Leight et al., "Direct measurement of matrix metalloproteinase activity in 3D cellular microenvironments using a fluorogenic peptide substrate" Biomaterials, pp. 7344-7352, vol. 34, No. 30 (Oct. 2013).
Fudala et al.,"Fluorescence Detection of MMP-9. I. MMP-9 Selectively Cleaves Lys-Gly-Pro-Arg-Ser-Leu-Ser-Gly-Lys Peptide", Curr Pharm Biotechnol., pp. 834-838, vol. 12, No. 5 (May 2011).

(Continued)

*Primary Examiner* — Shin Lin Chen
(74) *Attorney, Agent, or Firm* — Browdy and Neimark, P.L.L.C.

(57) ABSTRACT

The present invention relates to a genetically encoded FRET-based biosensor to monitor the activity of matrix metalloproteinase 9 (MMP-9). MMP-9 is an extracellular acting endopeptidase implicated in both physiological and pathological processes. A genetically encoded FRET biosensor anchored in the cellular membrane allows studying the proteolytic activity of MMP-9 with high spatiotemporal resolution at the exact region of MMP-9 action on the cell. Applicability of the biosensor, both in vitro and in vivo in living cells, has been demonstrated by ratiometric analysis of cleavage of the biosensor by a purified auto-activating mutant of MMP-9.

7 Claims, 5 Drawing Sheets

(56) References Cited

OTHER PUBLICATIONS

Fudala et al.,"Fluorescence Detection of MMP-9. II. Ratiometric FRET-Based Sensing With Dually Labeled Specific Peptide" Curr Pharm Biotechnol., pp. 1134-1138 vol. 14 (Aug. 2012).
Burdette et al.,"Fluorescent Sensors for Zn2+ Based on a Fluorescein Platform: Synthesis, Properties and Intracellular Distribution" J. Am. Chem. Soc. pp. 7831-7841, vol. 123 (Jan. 2001).
Hawkins et al., Fluorometric immunocapture assay for the specific measurement of matrix metalloproteinase-9 activity in biological samples: application to brain and plasma from rats with ischemic stroke, Molecular Brain pp. 1-11, vol. 6 No. 14 (Mar. 2013).
Schonbeck et al.,"Generation of Biologically Active IL-1b by Matrix Metalloproteinases: A Novel Caspase-1-Independent Pathway of IL-1b Processing", The Journal of Immunology, pp. 3340-3346, vol. 161 (Oct. 1998).
Li et al.,"Harnessing homologous recombination in vitro to generate recombinant DNA via SLIC", Nature Methods, pp. 251-256, vol. 4, No. 3 (Mar. 2007).
Sameni et al.,"Imaging and quantifying the dynamics of tumor-associated proteolysis", Clin Exp Metastasis, pp. 299-309, vol. 26, No. 4 (Apr. 2009).
Scherer et al.,"Imaging matrix metalloproteinases in cancer" Cancer Metastasis Rev, pp. 679-690, vol. 27 (May 2008).
Lam et al.,"Improving FRET dynamic range with bright green and red fluorescent proteins", Nat Methods, pp. 1005-1012, vol. 9, No. 10 (Oct. 2012).
Schmalfeldt et al.,"Increased Expression of Matrix Metalloproteinases (MMP)-2, MMP-9, and the Urokinase-Type Plasminogen Activator Is Associatedwith Progression from Benign to Advanced Ovarian Cancer", Clinical Cancer Research, pp. 2396-2404, vol. 7, (Aug. 2001).
Hanemaauer et al.,"Increased Gelatinase-A and Gelatinase-B Activities in Malignant Vs. Benign Breast Tumors", Int. J. Cancer, pp. 204-207, vol. 86, (Apr. 2000).
Cavallo-Medved et al.,"Live-cell imaging demonstrates extracellular matrix degradation in association with active aathepsin B in caveolae of endothelial cells during tube formation", Exp Cell Res., pp. 1234-1246, vol. 315, No. 7 (Apr. 2009).
Michaluk et al.,"Matrix Metalloproteinase-9 Controls NMDA Receptor Surface Diffusion through Integrin b1 Signaling", The Journal of Neuroscience, pp. 6007-6012, vol. 29, No. 18 (May 2009).
Deryugina et al.,"Matrix metalloproteinases and tumor metastasis", Cancer Metastasis Rev, pp. 9-34, vol. 25 (Mar. 2006).
Kessenbrock et al."Matrix Metalloproteinases: Regulators of the Tumor Microenvironment", Cell, pp. 52-67, vol. 141, No. 1 (Apr. 2010).
Kaijzel et al.,"Multimodality Imaging Reveals a Gradual Increase in Ma580trix Metalloproteinase Activity at Aneurysmal Lesions in Live Fibulin-4 Mice" Circ Cardiovasc Imaging, pp. 567-580, (Dec. 2009).
Wallisdevries et al.,"Multispectral Near-Infrared Fluorescence Molecular Multispectral Near-Infrared Fluorescence Molecular Imaging of Matrix Metalloproteinases in a Human Carotid Plaque Using a Matrix-Degrading Metalloproteinase-Sensitive Activatable Fluorescent Probe", NIRF Imaging of MMP, pp. 534-536, vol. 119 (May 2009).
Miranda et al., New Alternately Colored FRET Sensors for Simultaneous Monitoring of Zn2+ in Multiple Cellular Locations, PLoS One, pp. 1-10, vol. 7, No. 11 (Nov. 2012).
Lee et al.,"Optical imaging of MMP expression and cancer progression in an inflammation-induced colon cancer model", International Journal of Cancer, pp. 1846-1853, vol. 131, (Oct. 2012).
Ouyang et al.,"Visualization of Polarized Membrane Type 1 Matrix Metalloproteinase Activity in live Cells by Fluorescence Resonance Energy Transfer Imaging", Journal of Biological Chemistry, pp. 17740-17748, vol. 283, No. 25 (Jun. 2008).
Esposito et al., "pHlameleons: A Family of FRET-Based Protein Sensors for Quantitative pH Imaging", Biochemistry, pp. 13115-13126, vol. 47 (Oct. 2008).
Klein et al.,"Physiology and pathophysiology of matrix metalloproteases", Amino Acids, pp. 271-290, vol. 41 (Jul. 2011).
Pires-Alves et al.,"Tandem fluorescent proteins as enhanced FRET-based substrates for botulinum neurotoxin activity", Toxicon, pp. 392-399, vol. 53 (Jan. 2009).
Roy et al. "Potential of Fluorescent Metalloproteinase Substrates for Cancer Detection" Clin Biochem. pp. 1434-1439, vol. 44, No. 17-18 (Dec. 2011).
Zeug et al., Quantitative Intensity-Based FRET Approaches—A Comparative Snapshot, Biophysical Society, pp. 1821-1827, vol. 103 (Mar. 2012).
Evers et al.,"Quantitative Understanding of the Energy Transfer between Fluorescent Proteins Connected via Flexible Peptide Linkers", Biochemistry, pp. 13183-13192, vol. 45 (Jun. 2006).
Rafal et al.,"Fluorescence Detection of MMP-9. I. MMP-9 Selectively Cleaves Lys-Gly-Pro-Arg-Ser-Leu-Ser-Gly-Lys Peptide"Current Pharmaceutical Biotechnology, pp. 834-838, vol. 12, No. 5, (May 2011).
Kridel et al.,"Substrate Hydrolysis by Matrix Metalloproteinase-9", The Journal of Biological Chemistry, pp. 20572-20578, vol. 276, No. 23 (Jan. 2001).
Wang et al.,"Targeting Gelatinases with a Near-Infrared Fluorescent Cyclic His-Try-Gly-Phe Peptide", Mol Imaging Biol., pp. 424-433, vol. 11, No. 6 (Nov. 2009).
Kalab et al.,"The design of Förster (fluorescence) resonance energy transfer (FRET)-based molecular sensors for Ran GTPase", Methods, pp. 220-232, vol. 51 (Jan. 2010).
Klein et al.,"The possible role of matrix metalloproteinase (MMP)-2 and MMP-9 in cancer, e.g. acute leukemia", Critical Reviews in Oncology/Hematology, pp. 87-100, vol. 50 (2004).
Tsien,"Very long-term memories may be stored in the pattern of holes in the perineuronal net", PNAS, pp. 12456-12461, vol. 110, No. 30 (Jul. 2013).
Grenwald et al., Visualization of Glutamine Transporter Activities in Living Cells Using Genetically Encoded Glutamine Sensors, PLoS One, pp. 1-13, vol. 7, No. 6, (Jun. 2012).
Meng et al.,"Visualizing dynamic cytoplasmic forces with a compliance-matched FRET sensor", Journal of Cell Science, pp. 261-269, vol. 124 (Sep. 2010).
Yang et al., "Detection of MMP activity in living cells by a genetically encoded surface-displayed FRET sensor" Biochimica et Biophysica Acta, pp. 400-407, vol. 1773 (Mar. 2007).

\* cited by examiner

SEQUENCE LISTING

<160> NUMBER OF SEQ ID NOS: 29

<210> SEQ ID NO 1
<211> LENGTH: 49
<212> TYPE: DNA
<213> ORGANISM: Artificial Sequence
<220> FEATURE:
<223> OTHER INFORMATION: Venus1 forward primer
<220> FEATURE:
<221> NAME/KEY: misc_feature
<223> OTHER INFORMATION: Synthetic

<400> SEQUENCE: 1
ctggggccca gccggccaga tctcccggca tggtgagcaa gggcgagga          49

<210> SEQ ID NO 2
<211> LENGTH: 46
<212> TYPE: DNA
<213> ORGANISM: Artificial Sequence
<220> FEATURE:
<223> OTHER INFORMATION: Venus1 reverse primer
<220> FEATURE:
<221> NAME/KEY: misc_feature
<223> OTHER INFORMATION: Synthetic

<400> SEQUENCE: 2
tcctcgccct tgctcaccat gctagccttg tacagctcgt ccatgc          46

<210> SEQ ID NO 3
<211> LENGTH: 46
<212> TYPE: DNA
<213> ORGANISM: Artificial Sequence
<220> FEATURE:
<223> OTHER INFORMATION: Venus2 forward primer
<220> FEATURE:
<221> NAME/KEY: misc_feature
<223> OTHER INFORMATION: Synthetic

<400> SEQUENCE: 3
gcatggacga gctgtacaag gctagcatgg tgagcaaggg cgagga          46

<210> SEQ ID NO 4
<211> LENGTH: 46
<212> TYPE: DNA
<213> ORGANISM: Artificial Sequence
<220> FEATURE:
<223> OTHER INFORMATION: Venus2 reverse primer
<220> FEATURE:
<221> NAME/KEY: misc_feature
<223> OTHER INFORMATION: Synthetic

<400> SEQUENCE: 4
tcctcgccct tgctcaccat cttaagcttg tacagctcgt ccatgc          46

<210> SEQ ID NO 5
<211> LENGTH: 46
<212> TYPE: DNA
<213> ORGANISM: Artificial Sequence
<220> FEATURE:
<223> OTHER INFORMATION: mTFP1 forward primer
<220> FEATURE:
<221> NAME/KEY: misc_feature
<223> OTHER INFORMATION: Synthetic

<400> SEQUENCE: 5
gcatggacga gctgtacaag cttaagatgg tgagcaaggg cgagga          46

<210> SEQ ID NO 6

```
<211> LENGTH: 53
<212> TYPE: DNA
<213> ORGANISM: Artificial Sequence
<220> FEATURE:
<223> OTHER INFORMATION: mTFP1 reverse primer
<220> FEATURE:
<221> NAME/KEY: misc_feature
<223> OTHER INFORMATION: Synthetic

<400> SEQUENCE: 6
agatgagttt ttgttcgtcg acctgcagcc gcacttgtac agctcgtcca tgc      53

<210> SEQ ID NO 7
<211> LENGTH: 186
<212> TYPE: DNA
<213> ORGANISM: Artificial Sequence
<220> FEATURE:
<223> OTHER INFORMATION: Venus FP - mTFP1 linker (linker LN1)
<220> FEATURE:
<221> NAME/KEY: misc_feature
<223> OTHER INFORMATION: Synthetic

<400> SEQUENCE: 7
cttaagggat cccccccgctc tctctctaag cttaaaggag gaaccggtgg aactggagga   60
accggtggaa ctggaggaac cggtggaact ggaggaaccg gtggaactgg aggaaccggt  120
ggaactggag gaaccggtgg aactggagga accggtggaa ctggaggaac cggtggaact  180
cttaag                                                              186

<210> SEQ ID NO 8
<211> LENGTH: 183
<212> TYPE: DNA
<213> ORGANISM: Artificial Sequence
<220> FEATURE:
<223> OTHER INFORMATION: Venus FP - Venus FP linker (linker LN2)
<220> FEATURE:
<221> NAME/KEY: misc_feature
<223> OTHER INFORMATION: Synthetic

<400> SEQUENCE: 8
gctagcggtg gtagcggtgg tagcggtgct agtggtggtt ctggttctag aggtggttct   60
ggttctagag gtggttctgg ttctagaggt ggttctggtt ctagaggtgg ttctggttct  120
agaggtggtt ctggttctag aggtggttct ggttctagag gtggttctgg ttctagagct  180
agc                                                                 183

<210> SEQ ID NO 9
<211> LENGTH: 84
<212> TYPE: DNA
<213> ORGANISM: Artificial Sequence
<220> FEATURE:
<223> OTHER INFORMATION: alpha-helical linker with cleavage site
<220> FEATURE:
<221> NAME/KEY: misc_feature
<223> OTHER INFORMATION: Synthetic

<400> SEQUENCE: 9
cttaaggagg aggagatcag agaggccttc agagtgttcc ccagaagcct gagcctgaga   60
cacgtgatga ccaacctgct taag                                          84

<210> SEQ ID NO 10
<211> LENGTH: 24
<212> TYPE: PRT
<213> ORGANISM: Artificial Sequence
<220> FEATURE:
<223> OTHER INFORMATION: alpha-helical linker with cleavage site
```

```
<220> FEATURE:
<221> NAME/KEY: misc_feature
<223> OTHER INFORMATION: Synthetic

<400> SEQUENCE: 10

Glu Glu Glu Ile Arg Glu Ala Phe Arg Val Phe Pro Arg Ser Leu Ser
1               5                   10                  15

Leu Arg His Val Met Thr Asn Leu
            20

<210> SEQ ID NO 11
<211> LENGTH: 31
<212> TYPE: DNA
<213> ORGANISM: Artificial Sequence
<220> FEATURE:
<223> OTHER INFORMATION: mTFP1 forward primer
<220> FEATURE:
<221> NAME/KEY: misc_feature
<223> OTHER INFORMATION: Synthetic

<400> SEQUENCE: 11
aagaacgggc ccatggtgag caagggcgag g                              31

<210> SEQ ID NO 12
<211> LENGTH: 32
<212> TYPE: DNA
<213> ORGANISM: Artificial Sequence
<220> FEATURE:
<223> OTHER INFORMATION: mTFP1 reverse primer
<220> FEATURE:
<221> NAME/KEY: misc_feature
<223> OTHER INFORMATION: Synthetic

<400> SEQUENCE: 12
aagaacagat ctcttgtaca gctcgtccat gc                             32

<210> SEQ ID NO 13
<211> LENGTH: 62
<212> TYPE: PRT
<213> ORGANISM: Artificial Sequence
<220> FEATURE:
<223> OTHER INFORMATION: Venus FP - Venus FP linker (linker LN2)
<220> FEATURE:
<221> NAME/KEY: misc_feature
<223> OTHER INFORMATION: Synthetic

<400> SEQUENCE: 13

Leu Lys Gly Ser Pro Arg Ser Leu Ser Lys Leu Lys Gly Gly Thr Gly
1               5                   10                  15

Gly Thr Gly Gly Thr Gly Gly Thr Gly Gly Thr Gly Gly Thr Gly Gly
            20                  25                  30

Thr Gly Gly Thr Gly Gly Thr Gly Gly Thr Gly Gly Thr Gly Gly Thr
        35                  40                  45

Gly Gly Thr Gly Gly Thr Gly Gly Thr Gly Gly Thr Leu Lys
    50                  55                  60

<210> SEQ ID NO 14
<211> LENGTH: 61
<212> TYPE: PRT
<213> ORGANISM: Artificial Sequence
<220> FEATURE:
<223> OTHER INFORMATION: Venus FP - Venus FP linker (linker LN2)
<220> FEATURE:
<221> NAME/KEY: misc_feature
<223> OTHER INFORMATION: Synthetic

<400> SEQUENCE: 14
```

```
Ala Ser Gly Gly Ser Gly Gly Ser Ala Ser Gly Gly Ser Gly Ser
1               5                   10                  15

Arg Gly Gly Ser Gly Ser Arg Gly Gly Ser Gly Ser Arg Gly Ser
            20                  25                  30

Gly Ser Arg Gly Gly Ser Gly Ser Arg Gly Gly Ser Gly Ser Arg Gly
        35                  40                  45

Gly Ser Gly Ser Arg Gly Gly Ser Gly Ser Arg Ala Ser
    50                  55                  60

<210> SEQ ID NO 15
<211> LENGTH: 708
<212> TYPE: DNA
<213> ORGANISM: Artificial Sequence
<220> FEATURE:
<223> OTHER INFORMATION: mTFP1
<220> FEATURE:
<221> NAME/KEY: misc_feature
<223> OTHER INFORMATION: Synthetic

<400> SEQUENCE: 15
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc cccctgccc      180
ttctcctacg acattctgac caccgcgttc gcctacggca cagggccttt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acacctcaag ggcgagaact tccccccaa cggccccgtg      420
atgcagaaga gaccaccgg ctgggacgcc tccaccgaga ggatgtacgt gcgcgacggc     480
gtgctgaagg gcgacgtcaa gcacaagctg ctgctggagg cggcggccca ccaccgcgtt     540
gacttcaaga ccatctacag ggccaagaag gcggtgaagc tgcccgacta tcactttgtg     600
gaccaccgca tcgagatcct gaaccacgac aaggactaca caaggtgac cgtttacgag      660
agcgccgtgg cccgcaactc caccgacggc atggacgagc tgtacaag               708

<210> SEQ ID NO 16
<211> LENGTH: 236
<212> TYPE: PRT
<213> ORGANISM: Artificial Sequence
<220> FEATURE:
<223> OTHER INFORMATION: mTFP1
<220> FEATURE:
<221> NAME/KEY: misc_feature
<223> OTHER INFORMATION: Synthetic

<400> SEQUENCE: 16

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
```

```
                        85                  90                  95
Ser Trp Glu Arg Thr Met Thr Phe Glu Asp Lys Gly Ile Val Lys Val
                100                 105                 110
Lys Ser Asp Ile Ser Met Glu Glu Asp Ser Phe Ile Tyr Glu Ile His
            115                 120                 125
Leu Lys Gly Glu Asn Phe Pro Pro Asn Gly Pro Val Met Gln Lys Lys
        130                 135                 140
Thr Thr Gly Trp Asp Ala Ser Thr Glu Arg Met Tyr Val Arg Asp Gly
145                 150                 155                 160
Val Leu Lys Gly Asp Val Lys His Lys Leu Leu Leu Glu Gly Gly Gly
                165                 170                 175
His His Arg Val Asp Phe Lys Thr Ile Tyr Arg Ala Lys Lys Ala Val
                180                 185                 190
Lys Leu Pro Asp Tyr His Phe Val Asp His Arg Ile Glu Ile Leu Asn
            195                 200                 205
His Asp Lys Asp Tyr Asn Lys Val Thr Val Tyr Glu Ser Ala Val Ala
        210                 215                 220
Arg Asn Ser Thr Asp Gly Met Asp Glu Leu Tyr Lys
225                 230                 235

<210> SEQ ID NO 17
<211> LENGTH: 717
<212> TYPE: DNA
<213> ORGANISM: Artificial Sequence
<220> FEATURE:
<223> OTHER INFORMATION: Venus
<220> FEATURE:
<221> NAME/KEY: misc_feature
<223> OTHER INFORMATION: Synthetic

<400> SEQUENCE: 17
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcctgcag tgcttcgccc gctacccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccaa gctgagcaaa gaccccaacg agaagcgcga tcacatggtc     660
ctgctggagt tcgtgaccgc cgccgggatc actctcggca tggacgagct gtacaag       717

<210> SEQ ID NO 18
<211> LENGTH: 239
<212> TYPE: PRT
<213> ORGANISM: Artificial Sequence
<220> FEATURE:
<223> OTHER INFORMATION: Venus FP
<220> FEATURE:
<221> NAME/KEY: misc_feature
<223> OTHER INFORMATION: Synthetic

<400> SEQUENCE: 18
```

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

```
<210> SEQ ID NO 19
<211> LENGTH: 5325
<212> TYPE: DNA
<213> ORGANISM: Artificial Sequence
<220> FEATURE:
<223> OTHER INFORMATION: Plasmid pDisplay
<220> FEATURE:
<221> NAME/KEY: misc_feature
<223> OTHER INFORMATION: Synthetic

<400> SEQUENCE: 19
gcgcgcgttg acattgatta ttgactagtt attaatagta atcaattacg gggtcattag    60
ttcatagccc atatatggag ttccgcgtta cataacttac ggtaaatggc ccgcctggct   120
gaccgcccaa cgacccccgc ccattgacgt caataatgac gtatgttccc atagtaacgc   180
caatagggac tttccattga cgtcaatggg tggactattt acggtaaact gcccacttgg   240
cagtacatca agtgtatcat atgccaagta cgccccctat tgacgtcaat gacggtaaat   300
ggcccgcctg gcattatgcc cagtacatga ccttatggga ctttcctact tggcagtaca   360
tctacgtatt agtcatcgct attaccatgg tgatgcggt ttggcagtac atcaatgggc   420
gtggatagcg gtttgactca cggggatttc caagtctcca ccccattgac gtcaatggga   480
gtttgttttg gcaccaaaat caacgggact ttccaaaatg tcgtaacaac tccgccccat   540
tgacgcaaat gggcggtagg cgtgtacggt gggaggtcta taagcaga gctctctggc    600 taactagaga acccactgct tactggctta tcgaaattaa tacgactcac tataggaga    660
```

| | |
|---|---|
| cccaagcttg gtaccgagct cggatccact agtaacggcc gccagtgtgc tggaattcgg | 720 |
| cttggggata tccaccatgg agacagacac actcctgcta tgggtactgc tgctctgggt | 780 |
| tccaggttcc actggtgact atccatatga tgttccagat tatgctgggg cccagccggc | 840 |
| cagatctccc gggatccgcg gctgcaggtc gacgaacaaa aactcatctc agaagaggat | 900 |
| ctgaatgctg tgggccagga cacgcaggag gtcatcgtgg tgccacactc cttgcccttt | 960 |
| aaggtggtgg tgatctcagc catcctggcc ctggtggtgc tcaccatcat ctcccttatc | 1020 |
| atcctcatca tgctttggca gaagaagcca cgttaggcgg ccgctcgaga tcagcctcga | 1080 |
| ctgtgccttc tagttgccag ccatctgttg tttgccccctc cccgtgcctt ccttgaccc | 1140 |
| tggaaggtgc cactcccact gtcctttcct aataaaatga ggaaattgca tcgcattgtc | 1200 |
| tgagtaggtg tcattctatt ctggggggtg gggtggggca ggacagcaag ggggaggatt | 1260 |
| gggaagacaa tagcaggcat gctggggatg cggtgggctc tatggcttct gaggcggaaa | 1320 |
| gaaccagtgg cggtaatacg gttatccaca gaatcagggg ataacgcagg aaagaacatg | 1380 |
| tgagcaaaag gccagcaaaa ggccaggaac cgtaaaaagg ccgcgttgct ggcgtttttc | 1440 |
| cataggctcc gcccccctga cgagcatcac aaaaatcgac gctcaagtca gaggtggcga | 1500 |
| aacccgacag gactataaag ataccaggcg tttccccctg gaagctccct cgtgcgctct | 1560 |
| cctgttccga ccctgccgct taccggatac ctgtccgcct ttctcccttc gggaagcgtg | 1620 |
| gcgctttctc atagctcacg ctgtaggtat ctcagttcgg tgtaggtcgt tcgctccaag | 1680 |
| ctgggctgtg tgcacgaacc ccccgttcag cccgaccgct gcgccttatc cggtaactat | 1740 |
| cgtcttgagt ccaacccggt aagacacgac ttatcgccac tggcagcagc cactggtaac | 1800 |
| aggattagca gagcgaggta tgtaggcggt gctacagagt tcttgaagtg gtggcctaac | 1860 |
| tacggctaca ctagaaggac agtatttggt atctgcgctc tgctgaagcc agttaccttc | 1920 |
| ggaaaaagag ttggtagctc ttgatccggc aaacaaacca ccgctggtag cggtggtttt | 1980 |
| tttgtttgca agcagcagat tacgcgcaga aaaaaaggat ctcaagaaga tcctttgatc | 2040 |
| ttttctacgg ggtctgacgc tcagtggaac gaaaactcac gttaagggat tttggtcatg | 2100 |
| agattatcaa aaaggatctt cacctagatc cttttaaatt aaaaatgaag ttttaaatca | 2160 |
| atctaaagta tatatgagta acctgaggct atggcagggc ctgccgcccc gacgttggct | 2220 |
| gcgagccctg ggccttcacc cgaacttggg ggtgggggtg gggaaaagga agaaacgcgg | 2280 |
| gcgtattggc cccaatgggg tctcggtggg gtatcgacag agtgccagcc ctgggaccga | 2340 |
| accccgcgtt tatgaacaaa cgacccaaca ccgtgcgttt tattctgtct ttttattgcc | 2400 |
| gtcatagcgc gggttccttc cggtattgtc tccttccgtg tttcagttag cctcccccta | 2460 |
| gggtgggcga agaactccag catgagatcc ccgcgctgga ggatcatcca gccggcgtcc | 2520 |
| cggaaaacga ttccgaagcc caacctttca tagaaggcgg cggtggaatc gaaatctcgt | 2580 |
| gatggcaggt tgggcgtcgc ttggtcggtc atttcgaacc ccagagtccc gctcagaaga | 2640 |
| actcgtcaag aaggcgatag aaggcgatgc gctgcgaatc gggagcggcg ataccgtaaa | 2700 |
| gcacgaggaa gcggtcagcc cattcgccgc caagctcttc agcaatatca cgggtagcca | 2760 |
| acgctatgtc ctgatagcgg tccgccacac ccagccggcc acagtcgatg aatccagaaa | 2820 |
| agcggccatt ttccaccatg atattcggca agcaggcatc gccatgggtc acgacgagat | 2880 |
| cctcgccgtc gggcatgctc gccttgagcc tggcgaacag ttcggctggc gcgagcccct | 2940 |
| gatgctcttg atcatcctga tcgacaagac cggcttccat ccgagtacgt gctcgctcga | 3000 |

```
tgcgatgttt cgcttggtgg tcgaatgggc aggtagccgg atcaagcgta tgcagccgcc    3060
gcattgcatc agccatgatg gatactttct cggcaggagc aaggtgagat gacaggagat    3120
cctgccccgg cacttcgccc aatagcagcc agtcccttcc cgcttcagtg acaacgtcga    3180
gcacagctgc gcaaggaacg cccgtcgtgg ccagccacga tagccgcgct gcctcgtctt    3240
gcagttcatt cagggcaccg gacaggtcgg tcttgacaaa agaaccggg cgcccctgcg     3300 ctgacagccg gaacacggcg gcatcagagc agccgattgt ctgttgtgcc cagtcatagc    3360
cgaatagcct ctccacccaa gcggccggag aacctgcgtg caatccatct tgttcaatca    3420
tgcgaaacga tcctcatcct gtctcttgat cgatctttgc aaaagcctag gcctccaaaa    3480
aagcctcctc actacttctg gaatagctca gaggccgagg aggcggcctc ggcctctgca    3540
taaataaaaa aaattagtca gccatggggc ggagaatggg cggaactggg cggagttagg    3600
ggcgggatgg gcggagttag gggcgggact atggttgctg actaattgag atgcatgctt    3660
tgcatacttc tgcctgctgg ggagcctggg actttccac acctggttgc tgactaattg     3720
agatgcatgc tttgcatact tctgcctgct ggggagcctg ggactttcc acaccctaac     3780 tgacacacat tccacagctg gttctttccg cctcaggact cttccttttt caataaatca    3840
atctaaagta tatgtgagta aacttggtct gacagttacc aatgcttaat cagtgaggca    3900
cctatctcag cgatctgtct atttcgttca tccatagttg cctgactccc cgtcgtgtag    3960
ataactacga tacgggaggg cttaccatct ggccccagtg ctgcaatgat accgcgagac    4020
ccacgctcac cggctccaga tttatcagca ataaaccagc cagccggaag ggccgagcgc    4080
agaagtggtc ctgcaacttt atccgcctcc atccagtcta ttaattgttg ccgggaagct    4140
agagtaagta gttcgccagt taatagtttg cgcaacgttg ttgccattgc tacaggcatc    4200
gtggtgtcac gctcgtcgtt tggtatggct tcattcagct ccggttccca acgatcaagg    4260
cgagttacat gatcccccat gttgtgcaaa aaagcggtta gctccttcgg tcctccgatc    4320
gttgtcagaa gtaagttggc cgcagtgtta tcactcatgg ttatggcagc actgcataat    4380
tctcttactg tcatgccatc cgtaagatgc ttttctgtga ctggtgagta ctcaaccaag    4440
tcattctgag aatagtgtat gcggcgaccg agttgctctt gcccggcgtc aatacgggat    4500
aataccgcgc cacatagcag aactttaaaa gtgctcatca ttggaaaacg ttcttcgggg    4560
cgaaaactct caaggatctt accgctgttg agatccagtt cgatgtaacc cactcgtgca    4620
cccaactgat cttcagcatc ttttactttc accagcgttt ctgggtgagc aaaaacagga    4680
aggcaaaatg ccgcaaaaaa gggaataagg gcgacacgga aatgttgaat actcatactc    4740
ttcctttttc aatattattg aagcatttat cagggttatt gtctcatgag cggatacata    4800
tttgaatgta tttagaaaaa taaacaaata ggggttccgc gcacatttcc ccgaaaagtg    4860
ccacctgacg cgccctgtag cggcgcatta agcgcggcgg gtgtggtggt tacgcgcagc    4920
gtgaccgcta cacttgccag cgccctagcg cccgctcctt tcgctttctt cccttccttt    4980
ctcgccacgt tcgccggctt tccccgtcaa gctctaaatc gggggctccc tttagggttc    5040
cgatttagtg ctttacggca cctcgacccc aaaaaacttg attagggtga tggttcacgt    5100
agtgggccat cgccctgata dacgttttt cgcccttga cgttggagtc cacgttcttt      5160
aatagtggac tcttgttcca aactggaaca acactcaacc ctatctcggt ctattctttt    5220
gatttataag ggattttgcc gatttcggcc tattggttaa aaaatgagct gatttaacaa    5280
aaatttaacg cgaattttaa caaaatatta acgcttacaa tttac                    5325
```

<210> SEQ ID NO 20
<211> LENGTH: 150
<212> TYPE: DNA
<213> ORGANISM: Homo sapiens

<400> SEQUENCE: 20
gctgtgggcc aggacacgca ggaggtcatc gtggtgccac actccttgcc ctttaaggtg    60
gtggtgatct cagccatcct ggccctggtg gtgctcacca tcatctccct tatcatcctc   120
atcatgcttt ggcagaagaa gccacgttag                                    150

<210> SEQ ID NO 21
<211> LENGTH: 49
<212> TYPE: PRT
<213> ORGANISM: Homo sapiens

<400> SEQUENCE: 21

Ala Val Gly Gln Asp Thr Gln Glu Val Ile Val Val Pro His Ser Leu
1               5                   10                  15

Pro Phe Lys Val Val Val Ile Ser Ala Ile Leu Ala Leu Val Val Leu
            20                  25                  30

Thr Ile Ile Ser Leu Ile Ile Leu Ile Met Leu Trp Gln Lys Lys Pro
        35                  40                  45

Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Pro Leu Gly Leu Ala Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Pro Leu Phe Tyr Ser Val
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Lys Ile Pro Arg Thr Leu Thr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

```
<400> SEQUENCE: 25

Pro Leu Arg Leu Ser Trp
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Pro Arg Ala Val Ser Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Lys Gly Pro Arg Gln Ile Thr
1               5

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

Leu Lys Gly Ser Pro Arg Ser Leu Ser Lys Leu Lys Gly Gly Thr Gly
1               5                   10                  15

Gly Thr Leu Lys
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic

<400> SEQUENCE: 29

Leu Lys Gly Ser Pro Arg Ser Leu Ser Lys Leu Lys Gly Gly Ser Gly
1               5                   10                  15

Ser Arg Leu Lys
            20
```

GENETICALLY ENCODED FRET-BASED MMP-9 ACTIVITY BIOSENSOR AND USE THEREOF

A Sequence Listing in ASCII text file format of 21,527 bytes in size, created on Sep. 7, 2017, with the file name "2017-09-07SequenceListing_STAWARSKI1" is incorporated herein by reference.

The present invention relates to genetically encoded FRET-based matrix metalloproteinase 9 (MMP-9) activity biosensor and use thereof.

PRIOR ART

Advances in the elucidation of mechanisms governing basic cellular functions have allowed to shift the researchers' focus towards cellular dynamics and created a growing demand for methods that would be sensitive and sufficiently quick to track dynamic processes within living cells. In the area of subcellular spatiotemporal localization of macromolecules interactions, the Förster Resonance Energy Transfer (FRET) based approaches are particularly useful.

Recently a significant number and diversity of genetically encoded FRET based biosensors that have been developed. They can be used to study such diverse phenomena as ion concentration [Miranda et al., 2012; Burdette et al., 2001; Esposito et al. 2008], organic compound concentration [Gruenwald et al., 2012], GTPase activity [Kalab and Soderholm, 2010], protein phosphorylation [Violin et al., 2003] and mechanical stress within the cell [Meng, F. and F. Sachs, 2011]. Their advantage is the ability to track these phenomena in real time in living cells and organisms.

MMP-9 is an extracellularly secreted 92 kDa protease that belongs to a family of zinc- and calcium-dependent endopeptidases. It cleaves a number of extracellular matrix proteins and cell adhesion molecules. Large body of research indicates that MMP-9 plays a significant role in the development of cancer through its dual role of regulating angiogenesis and cleaving the extracellular matrix, thus enabling tumors to enter metastasis [Klein and Bischoff, 2011; Deryugina and Quigley, 2006; Kessenbrock et al., 2010]. An increase in MMP-9 expression was observed in a number of different tumors in comparison to healthy subjects with an apparent positive link between the tumor aggressiveness and the MMP-9 activity levels [Hanemaaijer et al., 2000; Schmalfeldt et al., 2001]. MMP-9 processing of the extracellular matrix may also lead to the release of cytokines and growth factors [Schonbeck, et al., 1998; Yu and Stamenkovic, 2000] that facilitate angiogenesis. In fact research points to MMP-9 activity levels being a possible prognostic factor in cancer (see Klein, et al., 2004, for a review).

Current research also points to MMP-9 as one of the key regulators in synaptic plasticity and, by extension, in processes that are believed to be dependent on synaptic plasticity—learning and memory. Synaptic plasticity is the ability to alter the connection strength between synapses within the brain.

Commonly employed methods of detecting the MMP-9 proteolytic activity such as DQ-gelatin (a gelatin derivative heavily tagged with fluorescein with its fluorescence almost completely quenched when intact—gelatinase activity results in an increase in fluorescence) or gel/in situ zymography do not allow to assess the localization of gelatinase activity with a high spatiotemporal resolution. Moreover, they are both gelatin-based and detect the activity of MMP-2, another member of the gelatinase subfamily of matrix metalloproteinases (along with MMP-9). Since the MMP-2 expression levels are much higher than those of MMP-9, the majority of cleavage detected by these methods comes from the proteolytic activity of MMP-2 rather than MMP-9. The other recently created fluorescent MMP-9 activity biosensors are completely synthetic [Fudala, et al., 2011; Akers, et al., 2012; Roopali Roy, et al., 2011; Hawkins, et al., 2013; Leight et al., 2013] and as such were intended to be used in a manner akin to DQ-gelatin.

DQ-protein (dye-quenched) substrates are widely used MMP-9 activity probes that are the available commercially. The DQ substrates are analogs of natural substrates that have been excessively tagged with fluorescent dyes. The close proximity of dye molecules caused by this excessive tagging is responsible for the quenching of the fluorescent signal of an intact substrate. Hydrolysis of the DQ substrate by MMP-9 leads to separation of the dye molecules and an increase in the fluorescence signal. DQ-gelatin and DQ-collagen IV have been successfully used to detect protease activity in vitro (gelatinase activity assay tests), on gel and in situ zymography and in live cell imaging microscopy as well (see Cavallo-Medved, et al., 2009 and Sameni, et al., 2009). The DQ-gelatin and DQ-collagen IV enabled the visualization of ECM degradation and intracellular tracking of degradation products in living cells. That, however, was the limit of their usefulness as the identification of proteases responsible for the degradation and cellular compartments that contained both these proteases and degradation products required additional techniques. DQ substrates offer at best only a global measure of proteolytic activity, even if used in conjunction with live cell imaging. Cleaved by multiple proteases, of little use when local, ultrastructural morphological changes are concerned and unsuitable for in vivo imaging, DQ-protein substrates will not facilitate future studies into fundamental physiological and pathological roles of MMP-9.

Therefore a number of new molecular probes have been designed that strive to tackle the insufficiencies of DQ-protein substrates. Because of the potential of MMPs as a prognostic markers of cancer, considerable work has been done in the area of diagnostic and analytical probes for the detection of the proteolytic activity of MMP-9 (see Roopali Roy, et al., 2011, for a survey of several MMP-9 activity probes and their suitability as a diagnostic tool to detect cancer and Scherer, et al., 2008 for a general review of the recent developments in the area of MMP activity detection in cancer). Near-infrared or NIRF probes have generated considerable interest thanks to the body permeability to the near-infrared light and thus a potential to be used in vivo, though positron emission tomography probes have also been developed. Many of the NIRF probes display self-quenching properties to increase the signal to noise ratio. A cyclic peptide NIRF probe called Cy5.5-C6 developed in 2009 [Wang, et al., 2009] and originally intended to detect MMP-2 activity was successfully used to correlate the progression of colorectal cancer with the levels of MMP-2 and MMP-9 [Lee, et al., 2012]. The unique property of that probe is that it binds to MMP-9 and inhibits its activity. The commercially available MMPSense 680 is another NIRF probe that was used to detect MMP-9 in vivo [Kaijzel, et al., 2010, and Wallis de Vries, et al., 2009], though the probe itself is fairly indiscriminate when it comes to protease specificity—it is cleaved by MMP-2, -3, -9 and -13. Finally by injecting mice carrying xenograft tumors with a self-assembling triple-helical near-infrared probe discussed in Akers, et al., 2012, researchers observed a robust (five-fold) increase in tumor-associated fluorescence 24 hour postinjection. The fluorescence was diminished with the administration of GM6001 broad-spectrum metalloproteinase inhibitor.

While the NIRF probes described above are a clear advance over DQ-protein substrates, they were designed with a much narrower scope in mind—as a diagnostic tool rather than a research one. Coupled with a low protease specificity displayed by some of them, undesirable MMP inhibitory properties of others and dependence on synthetic fluorochromes, it is obvious that they are not suitable for the localization of MMP-9 activity on the level of cellular ultrastructure (plasma membrane domains, dendritic spines, etc.).

The MMP-9 activity probe described in Fudala, et al., 2011 and Fudala, et al., 2012, solves the problem of low protease specificity by utilizing an artificial MMP-9 cleavage site. This analytical probe consists of two fluorescent dyes (5-FAM and Cy5) separated by a short peptide cleavable by MMP-9. In an intact probe the FRET causes the fluorescence of 5-FAM to be quenched and Cy5 fluorescence to be strongly enhanced. MMP-9 cleavage (but not MMP-2) results in the separation of fluorochromes and a significant increase in the fluorescence of 5-FAM. Though the MMP-9 activity probe developed by Fudala et al. is more than likely to be used in a clever way in the coming years (as was the case with DQ-protein substrates) it suffers from the same shortcoming as NIRF probes, which preclude it from being utilized to study fundamental roles of MMP-9 in physiological and pathological conditions.

Understanding various functions performed by MMP-9 in physiological (extracellular matrix remodeling, angiogenesis, synaptic plasticity) as well as pathological conditions (malignant progression of tumors, epilepsy) requires tools that would enable the assessment of its proteolytic activity. Recent years have witnessed the development of a number of functional imaging techniques that provide the means to measure and localize the MMP-9 activity in living cells. However, all of these methods depend on an exogenously applied fluorescent probe that can be cleaved by MMP-9. A genetically encoded, membrane-anchored, FRET-based MMP-9 activity biosensor might be better suited to elucidate the role of proteolytic activity of MMP-9 in physiological and pathological processes. Therefore, there exist a need to develop a biosensor that would enable investigation of the proteolytic activity of MMP-9 with high spatiotemporal resolution at the exact region of MMP-9 action on the cell that could be used both in vitro and in vivo in living cells.

INVENTION SUMMARY

The present invention provides a genetically encoded FRET-based MMP-9 activity biosensor that overcomes the limitations of the currently available biosensors and makes investigation of fundamental physiological and pathological roles of MMP-9 possible.

A genetically encoded MMP-9 activity biosensor of the invention comprises a FRET donor fluorescent protein and two FRET acceptor fluorescent proteins separated by flexible linkers, wherein the linker between the donor and acceptor proteins contains a synthetic MMP-9 cleavage site and the entire biosensor is anchored in the plasma membrane.

Preferably the FRET donor fluorescent protein in the biosensor of the invention is selected from a group comprising a monomeric teal fluorescent protein mTFP1 [Li and Elledge, 2007] and Clover fluorescent protein [Lam et al., 2012]. Most preferably the FRET donor fluorescent protein is mTFP1. mTFP1 is a protein generated from a tetrameric cyan fluorescent protein cFP484 isolated from the coral belonging to the genus *Clavularia*.

Preferably the FRET acceptor fluorescent protein is selected from a group comprising Venus Fluorescent Protein and mRuby2 fluorescent protein. Most preferably the FRET acceptor fluorescent protein is the Venus Fluorescent Protein. Venus Fluorescent Protein is an improved variant of the Yellow Fluorescent Protein.

The donor-acceptor FRET pair to be used in the biosensor of the invention should be characterized by high Förster radius and photostability.

The MMP-9 cleavage site in the biosensor of the invention preferably is a synthetic cleavage site. Examples of amino acid sequences that can be used as the MMP-9 cleavage site, i.e. these sequences that are capable of being cleaved by MMP-9, include PRSLS (residues 12-16 of SEQ ID NO:10) [Fudala, et al., 2011], PLGLAG (SEQ ID NO:22) [Tsien 2013], PLFYSV (SEQ ID NO:23), KIPRTLT (SEQ ID NO:24), PLRLSW (SEQ ID NO:25) and PRAVST (SEQ ID NO:26), KGPRQU (SEQ ID NO:27) [Kridel, et al., 2001]. The preferred MMP-9 cleavage site comprises PRSLS (residues 12-16 of SEQ ID NO:10) sequence.

In the preferred embodiment the biosensor of the invention is anchored in the plasma membrane by a transmembrane domain of the Platelet-derived growth factor receptor (PDGFR).

Preferably the flexible linkers in the biosensor of the invention are selected from a group consisting of an α-helical linker, a linker comprising one to eight repeats of GGTGGT (residues 13-18 of SEQ ID NO:13) hexapeptides, a linker comprising one to eight repeats of GGSGSR (residues 18-23 of SEQ ID NO:14) hexapeptides.

In one preferred embodiment, the linker between the donor protein and acceptor protein is the α-helical linker, which preferably comprises sequence EEEIREAFRVF-PRSLSLRHVMTNL (SEQ ID NO:10) (the site of α-helices is indicated in bold).

Alternatively the linker between the donor protein and acceptor protein, in addition to the MMP-9 cleavage site, comprises only one GGTGGT (residues 13-18 of SEQ ID NO:13) or GGSGSR (residues 18-23 of SEQ ID NO:14) hexapeptide and preferably it comprises only one GGTGGT (residues 13-18 of SEQ ID NO:13) hexapeptide. This linker is also referred to as a loop-like linker. In the most preferred embodiment, the linker consists of the following sequence: LKGSPRSLSKLK(GGTGGT/GGSGSR)LK (SEQ ID NOs: 28 and 29) (the MMP-9 cleavage site is indicated in bold).

The other linker, i.e. the linker between two acceptor proteins, comprises preferably seven repeats of GGSGSR (residues 18-23 of SEQ ID NO:14) hexapeptide.

The structures of the particularly preferred biosensors of the invention have been schematically presented in FIG. 1A. In one embodiment the biosensor of the invention comprises two Venus Fluorescent Proteins separated by a flexible linker comprising seven repeats of GGSGSR (residues 18-23 of SEQ ID NO:14) hexapeptide, wherein one of the Venus Fluorescent Proteins is separated from mTFP1 by an α-helical linker comprising a synthetic MMP-9 cleavage site. In other preferred embodiment the biosensor of the invention comprises two Venus Fluorescent Proteins separated by a flexible linker comprising seven repeats of GGSGSR (residues 18-23 of SEQ ID NO:14) hexapeptide, wherein one of the Venus Fluorescent Proteins is separated from mTFP1 by linker comprising a synthetic MMP-9 cleavage site and only one GGTGGT (residues 13-18 of SEQ ID NO:13) hexapeptide.

The biosensors of the invention exhibit high FRET efficiency and selectivity for MMP-9. The MMP-9 cleavage of the biosensor leads to the release of the acceptor proteins from the cell membrane and a decrease in FRET observed as a drop in the acceptor to donor fluorescence intensity ratio. Therefore, the invention also relates to the use of the genetically encoded MMP-9 activity biosensor of the invention as a system for investigation of the proteolytic activity of MMP-9 in vitro and in vivo in living cells.

DESCRIPTION OF THE FIGURES

FIG. 5A presents a map correlating the fluorescence intensity ratio values (OY axis) and fluorescence intensity in that pixel (OX axis). The map was generated for the cell presented in FIG. 5B. FIG. 5B presents images of a HEK293 cell taken at the indicated timepoints. Each pixel was assigned color and hue corresponding to the fluorescence intensity ratio of that pixel. Autoactivating MMP-9 was added to the culture at 5 min. A gradual decrease in the Venus/mTFP1 fluorescence intensity ratio was observed. FIG. 5C presents fluorescence intensity ratios of cells either mock treated, treated with inactive MMP-9 or autoactivating MMP-9. The values were normalized to an average fluorescence intensity ratio value calculated for timepoint before the start of the treatment. Each line represents an averaged ratio of 3 cells. The gradual decrease in the ratio values of cells treated with auto-activating MMP-9 was observed. No such decrease is observed in cells that were either mock treated or treated with inactive MMP-9. Error bars represent SEM values.

DETAILED DESCRIPTION

Figure 1:
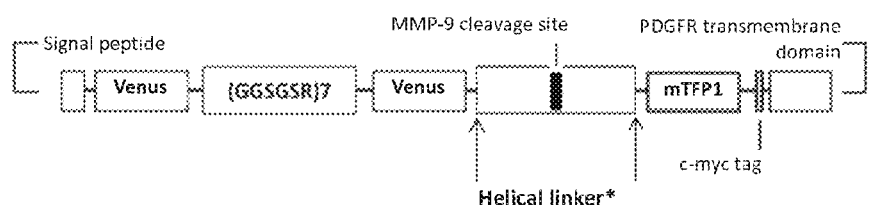
FIG. 1A presents the general structures of the preferred biosensors of the invention; in one embodiment (labeled (i)) Venus Fluorescent Proteins are separated by 7 GGSGSR (residues 18-23 of SEQ ID NO:14) repeats and Venus FP and mTFP1 by an α-helical linker comprising an MMP-9 cleavage site; in another embodiment (labeled (ii)) Venus Fluorescent Proteins are separated by 7 GGSGSR (residues 18-23 of SEQ ID NO:14) repeats and Venus FP and mTFP1 by MMP-9 cleavage site and 1 GGTGGT (residues 13-18 of SEQ ID NO:13) hexapeptide; variant sensors with lower number of hexapeptide repeats between fluorescent proteins were generated through partial cleavage of the genetic sequence of the sensor.
FIG. 1B presents FRET efficiency values calculated from AP; light gray bars indicate sensors analyzed with FLIM.
FIG. 1C presents live cell imaging of HEK293 expressing the biosensor of the invention.
FIG. 1D presents fractionation results of HEK293 cell line expressing the biosensor of the invention; WB against biosensor was carried out using anti-cmyc antibody; control WBs are presented below.
Figure 1:
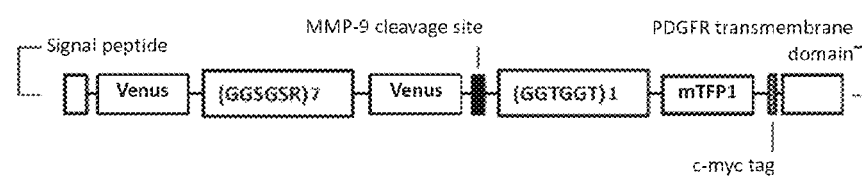
Figure 1:
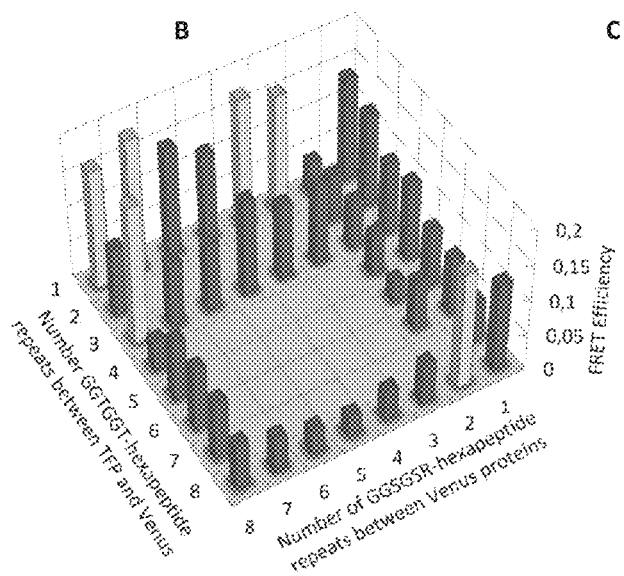
Figure 1:
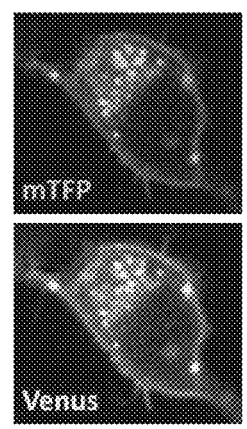
Figure 1:
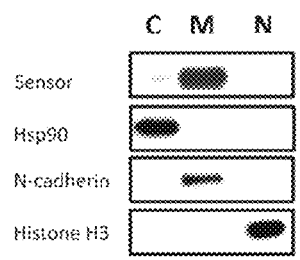

The genetically encoded FRET-based MMP-9 activity biosensor of the invention fills an important niche in the field of MMP-9 detection. Until now the MMP-9 activity probes were created with clinical diagnosis in mind, which is understandable, given the role of MMP-9 in the development of cancer. However, as recent years have shown, MMP-9 plays a critical role in other processes, for example in the physiology of the brain. Although probes, such as DQ-gelatin, have been incredibly useful in studying that aspect of MMP-9 role, they quite simply do not offer the required spatiotemporal resolution needed to answer numerous questions that have arisen. A genetically encoded, membrane-anchored FRET-based MMP-9 activity biosensor of the invention is better suited to elucidate the role of proteolytic activity of MMP-9 in physiological and pathological processes.

The biosensor of the invention utilizes a novel monomeric teal fluorescent protein (mTFP1) that possesses superior spectral properties to CFP [Day, et al., 2008]. It has previously been shown that mTFP1 forms a more efficient FRET pair with the Yellow Fluorescent Protein [Li and Elledge, 2007]. However, other fluorescent proteins, such as Clover FP [Lam et al., 2012], can also be used in the biosensor of the invention.

mTFP1 serves as a donor of energy while dual Venus Fluorescent Proteins serve as energy acceptors. Venus Fluorescent Protein, an improved variant of the Yellow Fluorescent Protein, was selected for the FRET acceptor. Other FP can also be used as acceptor FP, for example mRuby2 disclosed by Lam et al., supra.

Although the majority of FRET-based sensors contain one donor protein and one acceptor protein, two acceptor FP proteins were introduced into the sensor to increase its FRET efficiency. FRET efficiency of a single donor and single acceptor system is defined as:

$$E_1 = \frac{k_T}{k_T + k_R + k_F},$$

where $k_T$ is the energy transfer rate, $k_R$ is the rate constant of all other deactivation processes and $k_F$ is the fluorescence decay rate.

FRET efficiency of a single donor and two acceptors system is given by the following equation:

$$E_2 = \frac{2k_T}{2k_T + k_R + k_F}.$$

Introduction of a second acceptor in a FRET biosensor increases its FRET efficiency, since $$E_2 = \frac{2E_1}{1+E_1} \geq E_1.$$

The distance between fluorescent proteins in the biosensor of the invention was optimized to maximize the effective FRET efficiency. Since FRET efficiency is determined not only by the distance between the donor and acceptor proteins, but also by the orientation, flexible linkers formed from several GGSGGS (residues 18-23 of SEQ ID NO:14) or GGTGGT (residues 13-18 of SEQ ID NO:13) repeats were employed and proved to be efficient in improving the FRET efficiency. Two glycine residues give the linker its flexibility, while a larger amino acid determines linear distance between proteins.

The other factor determining the functionality of the biosensor of the invention is the MMP-9 cleavage sequence. A screen of known MMP-9 substrates has yielded neither a consensus sequence nor a secondary structure assumed by the MMP-9 cleavage site. Kridel et al. [Kridel, et al., 2001] reported a family of short peptides cleavable by MMP-9 using the phage display technology in an ELISA format. Thus the Inventors have selected a consensus sequence N'-PRSLS-C' suggested therein, which has been cloned into the biosensor of the invention. This sequence has previously been shown [Fudala et al., 2011] as being indeed recognized by MMP-9. However, other amino acid sequences can also be used as MMP-9 cleavage site (as it has been discussed above).

As the proteolytic cleavage efficiency strongly depends on the accessibility of the cleavage site, which in turn is influenced by its secondary and tertiary structures, the Inventors have decided to alter the structure of the linker positioned between mTFP1 and Venus Fluorescent Protein in the biosensor of the invention, by placing the MMP-9 cleavage site between two α-helices.

The Inventors have carried out the acceptor photobleaching (AP) experiments in order to rapidly screen generated biosensors and give a general indication of whether FRET occurs. These experiments were never intended to provide a reliable quantification of the FRET phenomenon. In-depth analysis of the FRET properties of biosensors with the highest FRET efficiency was performed with fluorescence lifetime imaging microscopy (FLIM). There is a slight discrepancy between FRET efficiency values calculated from AP and FLIM experiments. However, the FRET efficiency values based on AP are calculated for the entire cell (therefore they include the cytoplasm, where FRET is negligible due to the membranous localization of the biosensor), whereas FRET efficiency values based on FLIM measurements were calculated for much smaller regions, where FRET was most pronounced.

As the result of this analysis, it was found that the biosensor with α-helical linker has a higher FRET efficiency than the biosensor with a loop-like linker. This difference is likely due to different higher order structures assumed by loop-like and α-helical linkers, with the latter one being more compact and thus bringing the donor and acceptors closer to each other.

The MMP-9 proteolytic activity leads to the release of dual Venus proteins from the cell membrane and a decrease in the Venus to mTFP1 fluorescence ratio. The biosensor is present predominantly in the cell membrane. The presence of a small fraction of the biosensor in the cytoplasm may indicate some level of sensor degradation. The biosensor is cleaved by MMP-9 in an in vitro assay. The cleavage is not due to a spontaneous degradation of the protein and can be blocked by the addition of a broad spectrum MMP inhibitor. A baseline cleavage of the biosensor is observable in untreated lysate. Since cell lysis was performed without protease inhibitors of any kind, the observed cleavage may be caused by endogenous MMP-9 present in the HEK293 cell lysate. The baseline cleavage can be, at least partially, blocked by matrix metalloproteinase inhibitors—both broad-spectrum (GM6001 that blocks MMP-1, MMP-2, MMP-3, MMP-8 and MMP-9) and specific (Inhibitor I that selectively blocks MMP-9 and MMP-13).

The fluorescence emission spectra collected from cell membranes of fixed HEK293 cells expressing the biosensor and treated with the auto-activating MMP-9 differ from those recorded from untreated cells. The contribution of mTFP1 to the fluorescence signal increases, implying the cleavage of the biosensor. The effect of MMP-9 on the structure of biosensor has been followed with live cell imaging microscopy.

This shows usefulness of the biosensor of the invention for investigation of the proteolytic activity of MMP-9 in vitro, as well as in vivo in living cells.

EXAMPLES

Materials Used in the Examples

The genetically encoded FRET-based MMP-9 activity biosensor was assembled in the pDisplay plasmid (Clontech). The mTFP1 gene was amplified from the pmTFP1-N1 plasmid (Allele Biotech). The plasmid coding the Venus gene was provided by Jacek Jaworski (The International Institute of Cell Biology, Warsaw).

Phusion Hot Start II Polymerase was purchased from Thermo Scientific (formerly Finnzymes). XmaI, SacII, NheI, AflII, AgeI, XbaI, ApaI and BglII restriction enzymes were acquired in New England Biolabs and Thermo Scientific (formerly Fermentas). T4 DNA Polymerase required in the SLIC cloning was obtained from Thermo Scientific (formerly Fermentas). DMEM+GlutaMAX (High Glucose 4.5 g/L), Fetal Bovine Serum and penicillin/streptomycin mix were purchased from Sigma-Aldrich. Polyethylenoimine used for HEK293 cell line transfection was acquired from Fluka. Proteoextract Subcellular Proteome Kit was acquired from Calbiochem and EndoFree Plasmid DNA Maxi Kit from Qiagen. The α-GFP antibody was purchased from MBL (#498), the α-myc antibody from Santa Cruz Biotechnologies (#sc-40), the α-N-cadherin antibody from BD Biosciences (#610920), the α-hsp90 antibody from Stressgen (#SPS-771) and the α-histone H3 antibody from Abcam (#ab10799).

Poly-L-lysine used to coat glass cover slips was purchased from Sigma-Aldrich. The auto-activating MMP-9 was designed and purified as described previously [Michaluk, et al., 2007]. The oligonucleotides were ordered either at Sigma Aldrich or Genomed.

Example 1 Construction of MMP-9 Activity Biosensor (Loop-Type Linker)

The biosensor was cloned using the SLIC cloning methodology described in [Li, and Elledge, 2007]. The fluorescent protein genes were amplified with the Phusion Hot Start II High Fidelity Polymerase (Thermo Scientific) using the following primers:

```
Venus1
forward primer:
                                        (SEQ ID NO: 1)
CTGGGGCCCAGCCGGCCAGATCTCCCGGCATGGTGAG
CAAGGGCGAGGA reverse primer:
                                        (SEQ ID NO: 2)
TCCTCGCCCTTGCTCACCATGCTAGCCTTGTACAGCT
CGTCCATGC Venus2
forward primer:
                                        (SEQ ID NO: 3)
GCATGGACGAGCTGTACAAGGCTAGCATGGTGAGCAA
GGGCGAGGA reverse primer:
                                        (SEQ ID NO: 4)
TCCTCGCCCTTGCTCACCATCTTAAGCTTGTACAGCT
CGTCCATGC mTFP1
forward primer:
                                        (SEQ ID NO: 5)
GCATGGACGAGCTGTACAAGCTTAAGATGGTGAGCAA
GGGCGAGGA reverse primer:
                                        (SEQ ID NO: 6)
AGATGAGTTTTTGTTCGTCGACCTGCAGCCGCACTTG
TACAGCTCGTCCATGC.
```

The pDisplay plasmid was cleaved with XmaI and SacII enzymes to generate single stranded ends. Proper assembly of the Venus-Venus-mTFP1 tandem construct was confirmed using restriction enzyme analysis and sequencing.

Two restriction enzyme sites were introduced into the tandem construct: NheI site separated the Venus 1 and Venus2 fluorescent proteins, while AflII was cloned between the Venus2 and mTFP1 genes (sites marked in bold in primer sequences). Two oligonucleotides were cloned into these sites, each one coding a peptide linker designed to be flexible and provide spatial separation between the fluorescent proteins. Oligonucleotides were composed of repeated segments separated with restriction enzyme cleavage sites (AgeI and XbaI) to enable a rapid and simple adjustment of their length. An oligonucleotide (coding linker LN1) with the following sequence was cloned into the AflII site:

```
                                        (SEQ ID NO: 7)
CTTAAGGGATCCCCCCGCTCTCTCTCTAAGCTTAAA-
(GGAGGAACCGGTGGAACT)8-CTTAAG.
```

The AgeI restriction site is in bold font, the sequence coding the MMP-9 cleavage site was underlined. The following oligonucleotide (coding linker LN2) was cloned into the NheI site:

```
                                        (SEQ ID NO: 8)
GCTAGCGGTGGTAGCGGTGGTAGCGGtGCTAGT-(GG
TGGTTCTGGTTCTAGA)8-GCTAGC.
```

The XbaI restriction site is in bold. The biosensor constructed in the above fashion carried the MMP-9 cleavage site within an unstructured loop, hence the name: biosensor with a loop-like linker.

Example 2 Construction of MMP-9 Activity Biosensor (α-Helical Cleavage Site)

To construct a variant MMP-9 activity biosensor with the MMP-9 cleavage site located within α-helical structure, the linker between Venus and mTFP1 in biosensor with a loop-like linker was cut out with the AflII enzyme and replaced with the following oligonucleotide (SEQ NO ID: 9):

```
CTTAAGGAGGAGGAGATCAGAGAGGCCTTCAGAGTGT

TCCCCAGAAGCCTGAGCCTGAGACACGTGATGACCAA

CCTGCTTAAG
```

It encodes the following peptide (+1 Open Reading Frame): EEEIREAFRVFPRSLSLRHVMTNL (SEQ ID NO: 10), where sequences given in bold represent α-helices.

Example 3 Construction of Membrane Anchored mTFP1 Required for FLIM

The membrane anchored mTFP1 was constructed in the pDisplay plasmid. The mTFP1 gene was amplified with the following primers—

```
forward primer:
                                        (SEQ ID NO: 11)
AAGAACGGGCCCATGGTGAGCAAGGGCGAGG reverse primer:
                                        (SEQ ID NO: 12)
AAGAACAGATCTCTTGTACAGCTCGTCCATGC.
```

Given in bold are restriction sites—ApaI in forward primer and BglII in reverse primer, respectively. The PCR product was cloned between these sites into the pDisplay plasmid.

Example 4 Construction of MMP-9 Activity Biosensors with Varying Linker Lengths A series of variant biosensors with altered linker lengths were generated to perform FRET efficiency optimization for the biosensor. The plasmid coding the biosensor with full length linkers was subjected to partial cleavage with either AgeI or XbaI enzymes, religation and transformation into *E. coli*. Restriction enzyme cleavage reactions were performed with increasing amounts of enzyme. The LN1 linker was cleaved for 2 h with an amount of AgeI sufficient to cut from 1 to 4 of its restriction sites—0.85 U, 1 U, 1.5 U, 2 U, 2.5 U, 3 U, 3.5 U of AgeI were used. Similarly the LN2 linker was cleaved with 6 U, 8 U, 10 U, 12 U, 14 U, 16 U 18 U or 20 U for 2 h, to cleave the plasmid in 1 to 4 XbaI sites. Clones were analyzed using PCR to determine the linker length within the biosensors and sequenced.

The following biosensors were received: 1-1, 2-1, 3-1, 4-1, 5-1, 6-1, 7-1, 8-1, 1-2, 2-2, 8-2, 1-3, 2-3, 3-3, 4-3, 5-3, 6-3, 7-3, 8-3, 1-4, 2-4, 8-4, 1-5, 2-5, 8-5, 1-6, 2-6, 8-6, 1-7, 8-7, 1-8, 2-8, 3-8, 4-8, 5-8, 6-8, 7-8, 8-8, wherein the first digit in the number pair designating the biosensor variant indicates a number of GGSGGR (residues 18-23 of SEQ ID NO:14) hexapeptide repeats in LN2 linker and the second digit in the number pairs indicates a number of GGTGGT (residues 13-18 of SEQ ID NO:13) hexapeptide repeats in LN1 linker.

Example 5 Transfection of MMP-9 Activity Biosensors into HEK293 Cells

Routine FRET optimization and testing of the sensor were performed in the HEK293 cell line. Cells were cultured in DMEM (4.5 g/L glucose)+10% FBS+1% P/S in 37° C., 5% $CO_2$. Plasmids coding the sensors (identified in the proceeding Examples) were purified with the Qiagen Endo Free Plasmid Maxi Kit. DNA to be transfected was mixed with pure DMEM and polyethylenoimine (PEI) (5 µg/µL), left for 10 minutes at room temperature, and then transferred to cell culture. Cells were incubated with DNA-PEI complexes for 4 h, then the medium was replaced with a fresh one. Cells intended to be imaged on confocal microscope were cultured on glass cover slips coated with poly-L-lysine.

Example 6 AP/FLIM Analysis of the Cells Expressing MMP-9 Activity Biosensors Two days post transfection the cells obtained in Example 5 were fixed with 4% PFA, 3% sucrose in PBS and microscope slides were prepared. Acceptor photobleaching (AP) experiments were performed on Leica SP5 microscope with 63×NA (1.4) oil immersion objective. Images were acquired at 1024×1024 pixels. mTFP1 was imaged with the 458 nm line of an argon laser set to 20%. FRET efficiency of the sensors was determined by AP of the Venus with high power 514 nm laser and measuring the increase in the intensity of the fluorescence of mTFP1. Sensors determined to have highest FRET efficiency were further analyzed with the Fluorescence Lifetime Imaging Microscopy (FLIM) on Leica SP2 microscope.

The apparent FRET efficiency value of variant sensors from AP data was calculated using the following equation:

$$Ef_D = 1 - \left(\frac{F_{DA}}{F_D}\right), \quad (1)$$

where $f_D$ is the fraction of donor participating in the FRET complex, $F_{DA}$ and $F_D$ are the background subtracted and acquisition bleaching corrected pre- and post-bleach mTFP1 fluorescence intensities, respectively. The acquisition bleaching corrected post-bleach mTFP1 intensities were calculated as $$F_D = F_D^{B \cdot post} + \left(\frac{F_D^{R \cdot pre} - F_D^{R \cdot post}}{F_D^{R \cdot pre}}\right) F_D^{B \cdot pre}, \quad (2)$$

where $F_D^B$ and $F_D^R$ refer to mTFP1 intensities of the bleach and reference region of interest, and pre and post refer to pre-bleach and post-bleach measurements.

FRET efficiency values from FLIM data were calculated with the following equation $$Ef_D = \left(1 - \frac{\tau_D}{\tau_{DA}}\right)\frac{A_{DA}}{A_{DA} + A_D}, \quad (3)$$

where $\tau_D$ is the lifetime of the donor in the absence of the acceptor (in our case the membrane anchored mTFP1) and $\tau_{DA}$ is the lifetime of the FRET-based MMP-9 activity biosensor and $A_{DA}$ and $A_D$ represent the amplitude of individual decay components [Zeug, et al., 2012]. Error values were estimated using the Gaussian noise propagation equation $$stdE = \sqrt{\left(\frac{\partial E}{\partial \tau_D}\right)^2 \Delta \tau_D^2 + \left(\frac{\partial E}{\partial \tau_{DA}}\right)^2 \Delta \tau_{DA}^2}. \quad (4)$$

Example 7 Fluorescence Emission Spectra Collection for Cells Transfected with MMP-9 Activity Biosensors Lambda stack acquisition was performed on Zeiss LSM780 microscope equipped with 63×NA (1.4) oil-immersion objective at 1024×1024 pixels. The 458 nm line of an argon laser was used for excitation and 32 lambda channels were acquired, at 9 nm steps. Acquired lambda stacks were analysed with Fiji ImageJ software by measuring the average brightness of the plasma membrane in each channel. Recovered sensor spectra were normalized by having the area under the spectrum plot equaling 1.

Example 8 HEK293 Cell Fractioning

Cell fractioning experiments were performed using the Calbiochem ProteoExtract Subcellular Proteome Extraction kit. Sensor was detected on Western Blot using the anti-myc antibody. Quality of the cell fractioning was tested on Western Blot with the following antibodies: anti-hsp90, anti-N-cadherin and anti-histone H3.

Example 9 In Vitro Cleavage of the MMP-9 Activity Biosensors

Two days post-transfection HEK293 cells were washed one with PBS, scraped from the plate and lysed for 1 h at 4° C. with the following buffer: 50 mM Tris-Cl pH 7.5, 1% Triton X-100, 10 mM $CaCl_2$, 0.02% $NaN_3$, 1 µM $ZnCl_2$. The lysis was performed without protease inhibitors since it was feared that they might block the activity of our auto-activating MMP-9. The lysate was then centrifuged at 13400 rpm for 15' at 4° C. to remove cell debris. Equal amount of the cleared lysate were used in the subsequent reactions. Either 400 ng (final concentration 10 µg/mL), 1.2 µg (final concentration 30 µg/mL) of auto-activating MMP-9 or 400 ng (final concentration 10 µg/mL) of inactive MMP-9 were added to the reactions. GM6001 inhibitor was used in 25 µM final concentration. Reactions were stopped at either 30', 1 h, 4 h or after overnight incubation at 37° C. with the addition of SDS-PAGE Sample Buffer and heating to 100° C. for 10 minutes. Sensor was detected on Western Blot with the anti-GFP antibody.

Example 10 Cleavage of the MMP-9 Activity Biosensors in the Cell Culture

Two days post-transfection with the MMP-9 activity biosensors, the culture medium was replaced with pure DMEM. Cells were incubated for 30 min. with 400 ng of auto-activating MMP-9 (final concentration—800 ng/mL) and fixed with 4% PFA, 3% sucrose in PBS. Lambda stacks were acquired as previously described.

Example 12 Live Imaging—Ratiometric Analysis of Cells Transfected with MMP-9 Activity Bio Sensors The HEK293 cell line was cultured on Glass Bottom Microwell Dishes (MatTek Corporation). The cells were transfected with a plasmid coding the biosensor with α-helical liner. Two days post-transfection the cells were transferred to a Zeiss LSM780 microscope fitted with incubator and imaged using a water-immersion 40× objective. A single optical slice of the cells was captured at the 1024×1024 pixel resolution every 30 s with linear unmixing of the donor and acceptor fluorescence spectra performed in real time. Acquisition was performed for 30 min. 5 min after the start of image acquisition the cells were either mock treated with pure DMEM, auto-activating MMP-9 diluted in DMEM (final concentration—460 ng/mL) or inactive MMP-9 similarly diluted in DMEM to the same final concentration. Data analysis was performed in the custom written software under Matlab suite. The Venus/mTFP1 ratio was calculated for each pixel and plotted against the time elapsed from the start of the experiment.

Results

I. FRET Efficiency of the Biosensor (AP and FLIM Study)

The introduction of linkers with adjustable lengths allowed a rapid formation of 38 biosensor variants. Biosensors of the invention with the highest FRET efficiency were identified with the AP technique (FIG. 1B) and analyzed using FLIM to confirm AP-based FRET efficiency calculations.

Table 1 presents FRET Efficiency values calculated from FLIM data for the biosensors variants with the highest FRET efficiencies in AP experiments. Error values were estimated using the Gaussian noise propagation equation. The naming scheme of the variants is as follows: X-Y, where X—a number of hexapeptide repeats between both Venus FP (linker LN2), Y—a number of hexapeptide repeats between Venus FP and mTFP1 (linker LN1).

TABLE 1

FRET Efficiency of variant
FRET Efficiency of variant MMP-9 activity
biosensors with a loop-like linker - FLIM
Sensor variant

| 3-1 | 4-1 | 7-1 | 8-1 | 8-3 | 2-8 |
|---|---|---|---|---|---|
| 0.22 ± 0.05 | 0.22 ± 0.05 | 0.23 ± 0.05 | 0.19 ± 0.05 | 0.20 ± 0.05 | 0.22 ± 0.05 |

Figure 2:
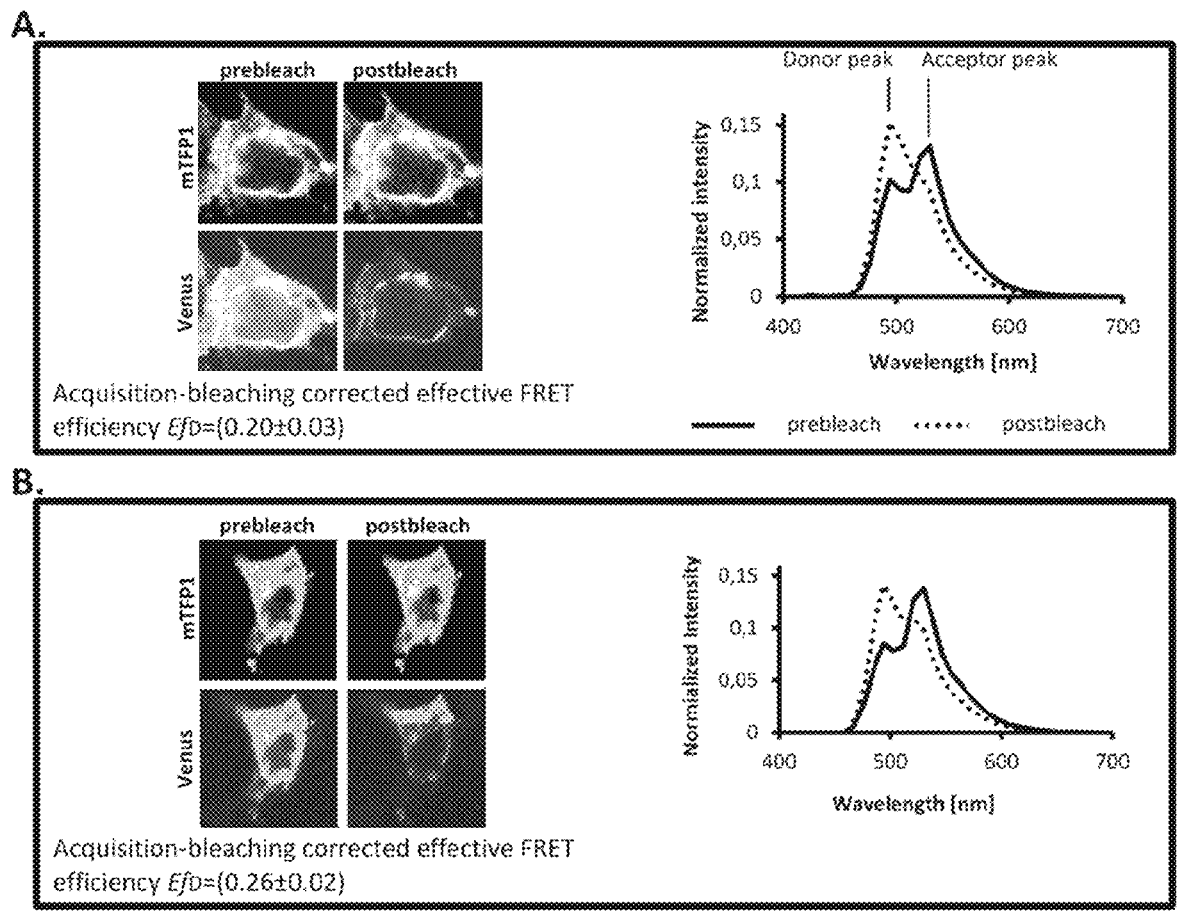
FIG. 2A presents images of HEK293 cells expressing the biosensor with a loop-like linker before and after AP; mTFP1 was excited with the 458 nm laser, Venus with 514 nm laser; right side of the panel presents emission spectra of the optimized biosensor before and after AP; the disappearance of the acceptor peak and the increased fluorescence intensity of the donor are visible.
FIG. 2B presents AP results of the biosensor having an α-helical linker.

A biosensor (named 7-1 in Table 1) with a long linker between the two Venus FP (seven repeats of GGTGGTTCTGGTTCTAGA (nucleotides 34-51 of SEQ ID NO:8) in its DNA sequence) and a short linker between the second Venus and mTFP1 (one GGAGGAACCGGTGGAACT (nucleotides 37-54 of SEQ ID NO:7) repeat in its DNA sequence) has the highest FRET efficiency of all obtained biosensor loop-like linker variants and the FRET efficiency was found to be E=0.20±0.03 (standard deviation value)—FIG. 2A. The biosensor with α-helical linker has a higher acquisition-bleaching corrected effective FRET efficiency 0.26±0.02 in comparison to the biosensor with the loop-like linker—FIG. 2B. Given the higher FRET efficiency exhibited by the biosensor with α-helical linker, it was used in further studies.

II. Cellular Membrane Localization

The MMP-9 activity biosensor of the invention localizes at the cellular membrane. This was confirmed by direct visualization of the biosensor in living HEK293 cells (FIG. 1C) and through cell fractionation followed by western blot analysis of collected fractions (FIG. 1D). Fractionation confirms that the vast majority (87%±6%) of the biosensor localizes in membranes with a small percentage in the cytoplasm. No biosensor was observed in the nucleus. Control western blots confirmed the purity of collected fractions.

III. In Vitro Biosensor Cleavage

Figure 3:
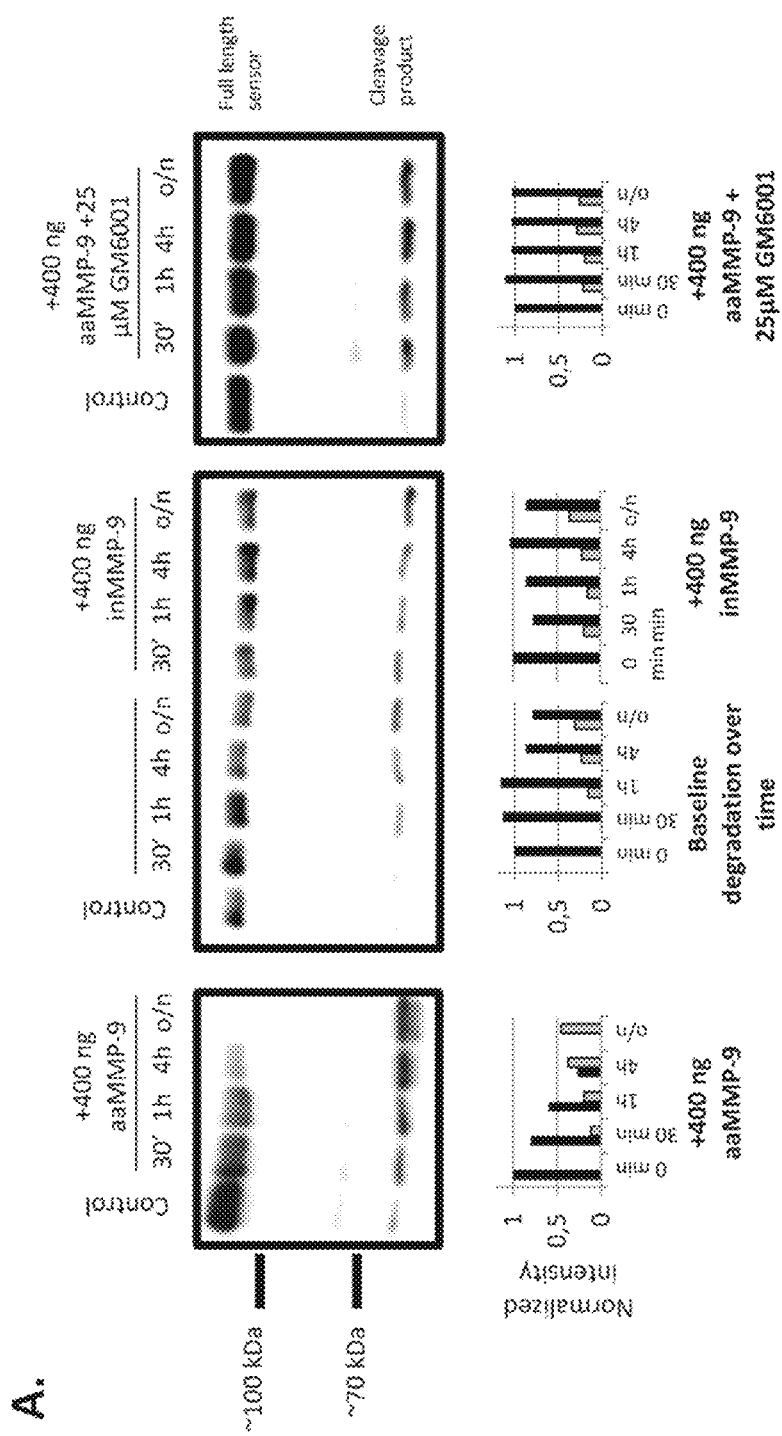
FIG. 3 presents in vitro cleavage of the sensor with an α-helical linker and negative controls—baseline cleavage, cleavage with the inactive MMP-9 and effects of GM6001 metalloproteinase inhibitor on the biosensor cleavage with the autoactivating MMP-9. Biosensor cleavage was analysed on WB with the anti-GFP antibody; on quantification plots intensity was normalized to full length biosensor in control lanes; intensity of the cleavage product in the control lane was subtracted from cleavage product intensities in the 30 min., 1 h, 4 h, o/n lanes prior to normalization.

The MMP-9 activity biosensor is cleaved in vitro by a human auto-activating MMP-9 (FIG. 3). Significantly more enzyme was used (standard concentration of auto-activating MMP-9 in experiments is 400 ng/mL [Michaluk et al., 2009]) in these reactions to make sure that the entire biosensor pool was cleaved.

The biosensor is already partially cleaved (14.2±0.4%—see FIG. 3B, control lanes; value normalized to full length biosensor intensity in control lanes) in transfected but otherwise untreated HEK293 cell line, which can be readily seen on the Western blot (FIG. 3). The in vitro cleavage of the biosensor with α-helical linker is not due to spontaneous degradation of the protein, though a slight increase in the amount of a cleaved form of the biosensor is observed over time (FIG. 3). Inactive human MMP-9 does not cleave the biosensor (FIG. 3). The cleavage can be blocked by the addition of a broad spectrum GM6001 matrix metalloproteinase inhibitor to the final concentration of 25 μM (FIG. 3).

Figure 4:
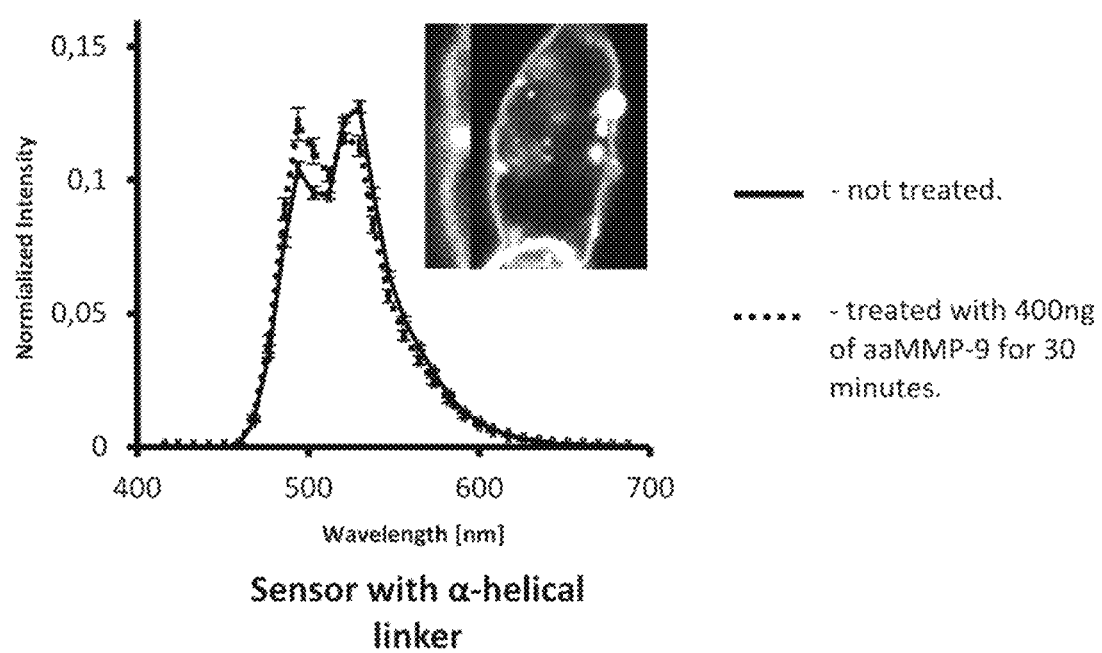
FIG. 4 presents spectra recorded for HEK293 cells expressing biosensor with an α-helical linker before and after the treatment with autoactivating MMP-9 (aaMMP-9); the treatment causes a spectrum shift towards shorter wavelengths indicating cleavage of the sensor. Error bars represent SEM values. Insert presents a maximum projection of a representative lambda stack of a HEK293 cell expressing the biosensor. A rectangle indicates an approximate region of interest, from which the emission spectrum was acquired. For each cell 3 ROIs were used to calculate the average emission spectrum.

IV. Biosensor Cleavage in the HEK293 Cell Culture—Fluorescence Emission Spectra of Fixed Cells Analysis of the fluorescence emission spectra collected from HEK293 cells incubated with the auto-activating MMP-9 for 30 minutes confirms that the biosensor is being cleaved in the cellular membrane (FIG. 4). The biosensor cleavage can be observed as a change in the emission spectrum of the biosensor within the membrane. The treatment with auto-activating MMP-9 results in a shift of the spectrum towards shorter wavelengths, a decrease in the contribution of Venus to the fluorescence signal (acceptor peak) and a corresponding increase in mTFP1 contribution (donor peak).

V. Biosensor Cleavage in the HEK293 Cell Culture—Live Cell Imaging

Figure 5:
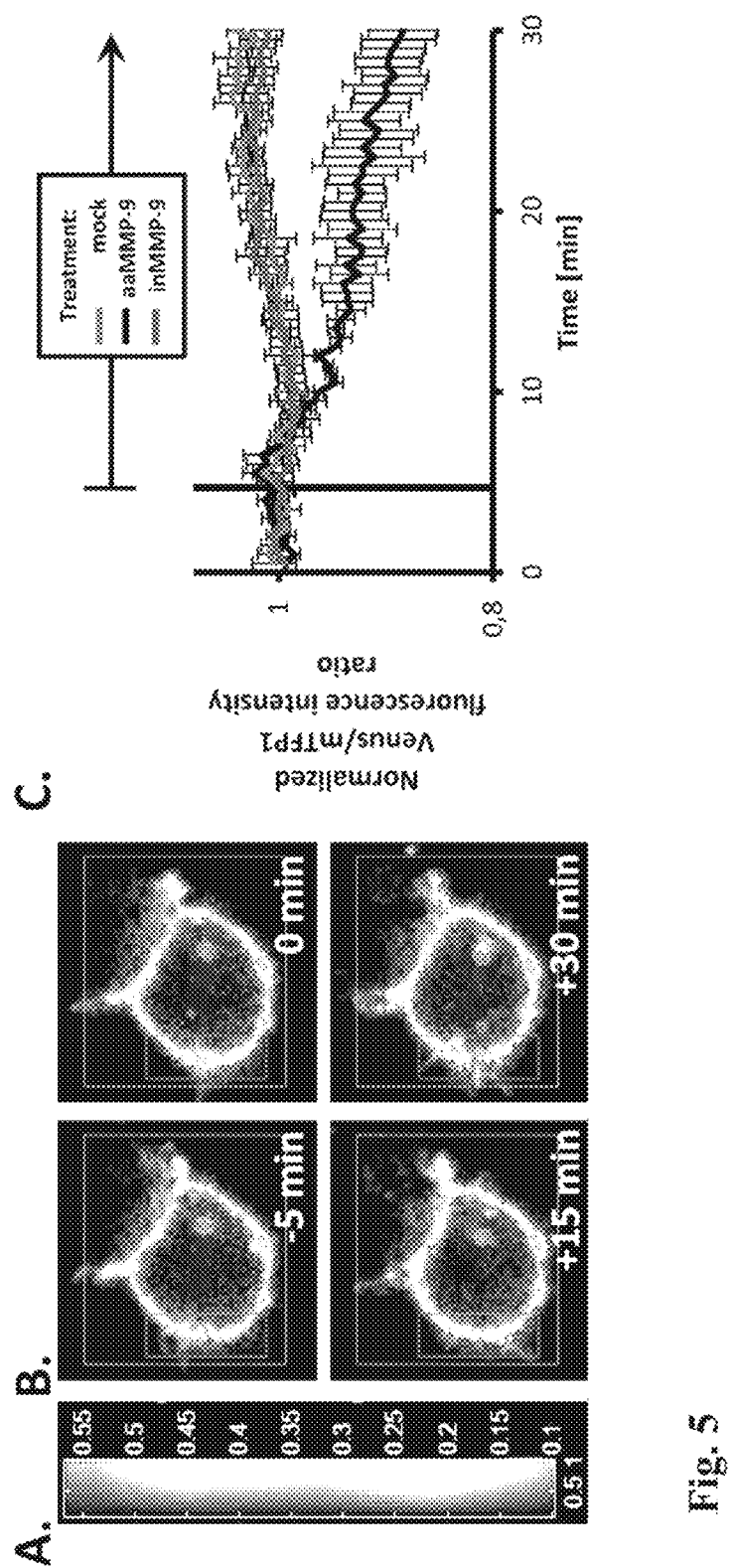
FIG. 5 presents images taken during live imaging of a HEK293 cells expressing the biosensor with α-helical linker. Linear unmixing was performed on cell images acquired on the Zeiss LSM780 to remove an influence of a spectral overlap between mTFP1 and Venus FP. The unmixed data was then used to calculate fluorescence intensity ratios for each pixel of the image in each timepoint of the experiment.

The cleavage of the biosensor can be observed in live imaging of HEK293 cells (FIG. 5) as a decrease of the Venus to mTFP1 fluorescence intensity ratio (FIG. 5). The addition of auto-activating MMP-9 to the culture medium results in a decrease in the ratio whereas mock treatment with pure medium or a treatment with inactive MMP-9 results in a slight, gradual increase (FIG. 5B).

REFERENCES

Akers, W. J., et al., *Detection of MMP-2 and MMP-9 Activity in Vivo with a Triple-Helical Peptide Optical Probe.* Bioconjugate Chemistry, 2012. 23(3): p. 656-663.

Burdette, S. C., et al., *Fluorescent Sensors for $Zn^{2+}$ Based on a Fluorescein Platform: Synthesis, Properties and Intracellular Distribution.* Journal of the American Chemical Society, 2001. 123(32): p. 7831-7841.

Cavallo-Medved, D., et al., *Live-cell imaging demonstrates extracellular matrix degradation in association with* active cathepsin B in caveolae of endothelial cells during tube formation. Experimental Cell Research, 2009. 315 (7): p. 1234-1246.

Day, R. N., C. F. Booker, and A. Periasamy, *Characterization of an improved donor fluorescent protein for Forster resonance energy transfer microscopy*. Journal of Biomedical Optics, 2008. 13(3): p. 031203-031203.

Deryugina, E. I. and J. P. Quigley, *Matrix metalloproteinases and tumor metastasis*. Cancer metastasis reviews, 2006. 25(1): p. 9-34.

Esposito, A., et al., *pHlameleons: A Family of FRET-Based Protein Sensors for Quantitative pH Imaging*. Biochemistry, 2008. 47 (49): p. 13115-13126.

Evers, T. H., et al., *Quantitative Understanding of the Energy Transfer between Fluorescent Proteins Connected via Flexible Peptide Linkers*. Biochemistry, 2006. 45(44): p. 13183-13192.

Fudala, R., et al., *Fluorescence detection of MMP-9. I. MMP-9 selectively cleaves Lys-Gly-Pro-Arg-Ser-Leu-Ser-Gly-Lys peptide*. Current pharmaceutical biotechnology, 2011. 12(5): p. 834-838.

Fudala R, R. R., Mukerjee A, Ranjan A P, Vishwanatha J K, Kurdowska A K, Gryczynski Z, Borejdo J, Gryczynski I, *Fluorescence Detection of MMP-9.11. Ratiometric FRET-Based Sensing With Dually Labeled Specific Peptide*. Current pharmaceutical biotechnology, 2012.

Gruenwald, K., et al., *Visualization of Glutamine Transporter Activities in Living Cells Using Genetically Encoded Glutamine Sensors*. PLoS ONE, 2012. 7(6): p. e38591.

Hanemaaijer, R., et al., *Increased gelatinase-A and gelatinase-B activities in malignant vs. benign breast tumors*. International Journal of Cancer, 2000. 86(2): p. 204-207.

Hawkins, K. E., et al., *Fluorometric immunocapture assay for the specific measurement of matrix metalloproteinase-9 activity in biological samples: application to brain and plasma from rats with ischemic stroke*. Molecular brain, 2013. 6: p. 14.

Kaijzel, E. L., et al., *Multimodality Imaging Reveals a Gradual Increase in Matrix Metalloproteinase Activity at Aneurysmal Lesions in Live Fibulin-4 Mice*. Circulation: Cardiovascular Imaging, 2010. 3(5): p. 567-577.

Kalab, P. and J. Soderholm, *The design of Forster (fluorescence) resonance energy transfer (FRET)-based molecular sensors for Ran GTPase*. Methods, 2010. 51(2): p. 220-232.

Kessenbrock, K., V. Plaks, and Z. Werb, *Matrix metalloproteinases: regulators of the tumor microenvironment*. Cell, 2010. 141(1): p. 5267.

Klein, G, et al., *The possible role of matrix metalloproteinase (MMP)-2 and MMP-9 in cancer, e.g. acute leukemia*. Crit Rev Oncol Hematol, 2004. 50(2): p. 87-100.

Klein, T. and R. Bischoff, *Physiology and pathophysiology of matrix metalloproteases*. Amino acids, 2011. 41(2): p. 271-90.

Kridel, S. J., et al., *Substrate Hydrolysis by Matrix Metalloproteinase-9\**. Journal of Biological Chemistry, 2001. 276(23): p. 20572-20578.

Lam A. J., St-Pierre F., Gong Y., Marshall J. D., Cranfill P. J., Baird M. A., McKeown M. R., Wiedenmann J, Davidson M. W., Schnitzer M. J., Tsien R. Y., Lin M. Z. Improving FRET dynamic range with bright green and red fluorescent proteins, Nat Methods. 2012. 9(10): p. 1005-1012.

Lee, C.-M., et al., *Optical imaging of MMP expression and cancer progression in an inflammation-induced colon cancer model*. International Journal of Cancer, 2012. 131(8): p. 1846-1853.

Leight, J. L., et al., *Direct measurement of matrix metalloproteinase activity in 3D cellular micro environments using a fluorogenic peptide substrate*. Biomaterials, 2013. 34(30): p. 7344-7352.

Li, M. Z. and S. J. Elledge, *Harnessing homologous recombination in vitro to generate recombinant DNA via SLIC*. Nat Meth, 2007. 4(3): p. 251-256.

Meng, F. and F. Sachs, *Visualizing dynamic cytoplasmic forces with a compliance-matched FRET sensor*. Journal of Cell Science, 2011. 124 (2): p. 261-269.

Michaluk, P., et al., *β-Dystroglycan as a Target for MMP-9, in Response to Enhanced Neuronal Activity*. Journal of Biological Chemistry, 2007. 282 (22): p. 16036-16041.

Michaluk, P., et al., *Matrix Metalloproteinase-9 Controls NMDA Receptor Surface Diffusion through Integrin β 1 Signaling*. The Journal of Neuroscience, 2009. 29(18): p. 6007-6012.

Miranda, J. G, et al., *New Alternately Colored FRET Sensors for Simultaneous Monitoring of $Zn^{2+}$ in Multiple Cellular Locations*. PLoS ONE, 2012. 7(11): p. e49371.

Ning, C., *Design Genetic Fluorescent Probes to Detect Protease Activity and Calcium-Dependent Protein-Protein Interactions in Living Cells*. Chemistry Dissertations of Georgia State University, 2008.

Roopali Roy, D. Z., Susan Pories, Marcia L. Moss and Marsha A. Moses, *Potential of Fluorescent Metalloproteinase Substrates for Cancer Detection*. Clinical Biochemistry, 2011. 44(17-18): p. 1434-1439.

Sameni, M., et al., *Imaging and quantifying the dynamics of tumor-associated proteolysis*. Clin Exp Metastasis, 2009. 26(4): p. 299-309.

Scherer, R., J. O. McIntyre, and L. Matrisian, *Imaging matrix metalloproteinases in cancer*. Cancer and Metastasis Reviews, 2008. 27 (4): p. 679-690.

Schmalfeldt, B., et al., *Increased Expression of Matrix Metalloproteinases (MMP)-2, MMP-9, and the Urokinase-Type Plasminogen Activator Is Associated with Progression from Benign to Advanced Ovarian Cancer*. Clinical Cancer Research, 2001. 7(8): p. 2396-2404.

Schonbeck, U., F. Mach, and P. Libby, *Generation of Biologically Active IL-1β by Matrix Metalloproteinases: A Novel Caspase-1-Independent Pathway of IL-1β Processing*. The Journal of Immunology, 1998. 161(7): p. 3340-3346.

Tsien R. Y., *Very long-term memories may be stored in the pattern of holes in the perineuronal net*, PNAS Early Edition. 2013 www.pnas.org/cgi/doi/10.1073/pnas.1310158110.

Violin, J. D., et al., *A genetically encoded fluorescent reporter reveals oscillatory phosphorylation by protein kinase C*. The Journal of Cell Biology, 2003. 161(5): p. 899-909.

Wallis de Vries, B. M., et al., *Multispectral Near-Infrared Fluorescence Molecular Imaging of Matrix Metalloproteinases in a Human Carotid Plaque Using a Matrix-Degrading Metalloproteinase-Sensitive Activatable Fluorescent Probe*. Circulation, 2009. 119(20): p. e534-e536.

Wang, W., et al., *Targeting Gelatinases with a Near-Infrared Fluorescent Cyclic His-Try-Gly-Phe Peptide*. Molecular Imaging and Biology, 2009. 11(6): p. 424-433.

Yu, Q. and I. Stamenkovic, *Cell surface-localized matrix metalloproteinase-9 proteolytically activates TGF-β and promotes tumor invasion and angiogenesis*. Genes & Development, 2000. 14 (2): p. 163-176.

Zeug, A., et al., *Quantitative Intensity-Based FRET Approaches A Comparative Snapshot*. Biophysical journal, 2012. 103(9): p. 18211827.

The invention claimed is:

1. A genetically encoded matrix metalloproteinase 9 (MMP-9) activity biosensor that is anchored in the plasma membrane comprising the teal fluorescent protein mTFP1 as a Förster Resonance Energy Transfer (FRET) donor fluorescent protein and two Venus Fluorescent Proteins as FRET acceptor fluorescent proteins all separated by flexible linkers, wherein
the two Venus Fluorescent Proteins are separated by a flexible linker comprising seven repeats of GGSGSR (residues 18-23 of SEQ ID NO:14) hexapeptide, and
one of the Venus Fluorescent Proteins is separated from the teal fluorescent protein mTFP1 by an α-helical linker comprising a synthetic MMP-9 cleavage site or a linker comprising a synthetic MMP-9 cleavage site and only one GGTGGT (residues 13-18 of SEQ ID NO:13) hexapeptide.

2. The biosensor of claim 1, wherein one of the Venus Fluorescent Proteins is separated from the teal fluorescent protein mTFP1 by α-helical linker comprising sequence EEEIREAFRVFPRSLSLRHVMTNL (SEQ ID NO:10).

3. The biosensor of claim 2, wherein the synthetic MMP-9 cleavage site corresponds to PRSLS sequence.

4. The biosensor of claim 2, wherein said biosensor is anchored in the plasma membrane by a PDGFR transmembrane domain.

5. The biosensor of claim 1, wherein the synthetic MMP-9 cleavage site corresponds to PRSLS (residues 12-16 of SEQ ID NO:10) sequence.

6. The biosensor of claim 5, wherein said biosensor is anchored in the plasma membrane by a PDGFR transmembrane domain.

7. The biosensor of claim 1, wherein said biosensor is anchored in the plasma membrane by a platelet-derived growth factor receptor (PDGFR) transmembrane domain.

\* \* \* \* \*